(12) United States Patent
Sakamoto et al.

(10) Patent No.: US 9,447,059 B2
(45) Date of Patent: Sep. 20, 2016

(54) INTERMEDIATE FOR MANUFACTURE OF POLYMERIZABLE COMPOUND AND PROCESS FOR MANUFACTURE THEREOF

(75) Inventors: Kei Sakamoto, Tokyo (JP); Kumi Okuyama, Tokyo (JP); Yasushi Nakano, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 14/347,962

(22) PCT Filed: Apr. 27, 2012

(86) PCT No.: PCT/JP2012/061323
§ 371 (c)(1),
(2), (4) Date: Apr. 25, 2014

(87) PCT Pub. No.: WO2013/046781
PCT Pub. Date: Apr. 4, 2013

(65) Prior Publication Data
US 2014/0235857 A1     Aug. 21, 2014

(30) Foreign Application Priority Data

Sep. 27, 2011   (JP) ................. 2011-211581
Feb. 27, 2012   (JP) ................. 2012-039648

(51) Int. Cl.
| C07D 277/82 | (2006.01) |
| C07D 237/34 | (2006.01) |
| C07D 215/38 | (2006.01) |
| C07D 263/58 | (2006.01) |
| C07C 251/86 | (2006.01) |
| G02B 5/30 | (2006.01) |

(52) U.S. Cl.
CPC .......... *C07D 277/82* (2013.01); *C07C 251/86* (2013.01); *C07D 215/38* (2013.01); *C07D 237/34* (2013.01); *C07D 263/58* (2013.01); *G02B 5/3083* (2013.01)

(58) Field of Classification Search
CPC  C07D 277/82; C07D 237/34; C07D 215/38; C07D 263/58; C07C 251/86
See application file for complete search history.

(56) References Cited

U.S. PATENT DOCUMENTS

| 5,506,331 | A | * | 4/1996 | Nagao et al. ............ 528/193 |
| 5,567,349 | A | | 10/1996 | Kelly et al. |
| 6,139,771 | A | | 10/2000 | Walba et al. |
| 6,203,724 | B1 | | 3/2001 | Reiffenrath et al. |
| 6,565,974 | B1 | | 5/2003 | Uchiyama et al. |
| 2002/0159005 | A1 | | 10/2002 | Arakawa et al. |
| 2003/0102458 | A1 | | 6/2003 | Nishikawa et al. |
| 2007/0176145 | A1 | | 8/2007 | Nishikawa et al. |
| 2007/0298191 | A1 | | 12/2007 | Yamahara et al. |
| 2009/0072194 | A1 | | 3/2009 | Yamahara et al. |
| 2009/0189120 | A1 | | 7/2009 | Takeuchi |

| 2010/0201920 | A1 | 8/2010 | Adlem et al. |
| 2010/0301271 | A1 | 12/2010 | Adlem et al. |
| 2011/0306489 | A1 | 12/2011 | Hikazudani et al. |

FOREIGN PATENT DOCUMENTS

| BE | 561091 | * 10/1957 |
| EP | 2143710 A1 | 1/2010 |

(Continued)

OTHER PUBLICATIONS

Carvalho et al. Bioorg. Med. Chem. 2008, 16, 413-421.*
CAS Registry Entry No. 330987-66-1, which entered STN on Apr. 12, 2001.*
CAS Registry Entry No. 412957-12-1, which entered STN on May 9, 2002.*
CAS Registry Entry No. 458549-52-5, which entered STN on Oct. 3, 2002.*
CAS Registry Entry No. 860294-91-3, which entered STN on Aug. 15, 2005.*
CAS Registry Entry No. 873295-00-2, which entered STN on Feb. 2, 2006.*

(Continued)

*Primary Examiner* — Matthew Coughlin
(74) *Attorney, Agent, or Firm* — Birch, Stewart, Kolasch & Birch, LLP

(57) ABSTRACT

The present invention pertains to a compound represented by a formula (I) and a method for producing thereof (in the formula, $A^x$ is an organic group having 2 to 30 carbon atoms that includes at least one aromatic ring selected from a group consisting of an aromatic hydrocarbon ring and an aromatic hetero ring, $A^y$ is a hydrogen atom, an alkyl group having 1 to 18 carbon atoms, a cycloalkyl group, an alkenyl group having 2 to 18 carbon atoms, an organic group having 2 to 30 carbon atoms that includes at least one aromatic ring selected from a group consisting of an aromatic hydrocarbon ring and an aromatic hetero ring, or the like. $A^x$ and $A^y$ optionally bond to each other to form a ring, and Q is a hydrogen atom, an alkyl group having 1 to 6 carbon atoms, or the like.). According to the invention, provided are a novel compound that makes it possible to produce an optical film that achieves uniform conversion of polarized light over a wide wavelength band can be inexpensively produced in high yield by utilizing the compound according to one aspect of the invention as an intermediate for producing the polymerizable compound, and a method for producing thereof.

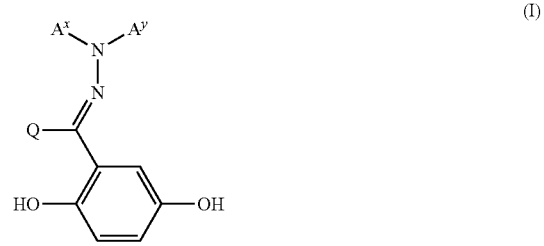

9 Claims, No Drawings

(56) References Cited

FOREIGN PATENT DOCUMENTS

| JP | 10-68816 A | 3/1998 |
|---|---|---|
| JP | 10-90521 A | 4/1998 |
| JP | 11-52131 A | 2/1999 |
| JP | 2001-4837 A | 1/2001 |
| JP | 2002-267838 A | 9/2002 |
| JP | 2005-208414 A | 8/2005 |
| JP | 2005-208415 A | 8/2005 |
| JP | 2005-208416 A | 8/2005 |
| JP | 2010-31223 A | 2/2010 |
| JP | 2010-70505 A | 4/2010 |
| JP | 2010-194518 A | 9/2010 |
| JP | 2011-6360 A | 1/2011 |
| JP | 2011-6361 A | 1/2011 |
| JP | 2011-42606 A | 3/2011 |
| WO | WO 01/68611 A1 | 9/2001 |
| WO | WO 2010/098245 A1 | 9/2010 |
| WO | WO 2011/020883 A1 | 2/2011 |

OTHER PUBLICATIONS

El-Tabl et al. Journal of the Korean Chemical Society 2011, 55, 19-27.*
Hanna et al. Bioorganic Chemistry 2007, 35, 50-58.*
CAS Registry Entry No. 1260138-05-3, which entered STN on Jan. 20, 2011.*
CAS Registry Entry No. 1348865-55-3, which entered STN on Dec. 5, 2011.*
CAS Registry Entry No. 1354403-03-4, which entered STN on Jan. 25, 2012.*
CAPLUS Entry for German Patent Document No. DD 160762 A3, which was published in 1984.*
CAS Registry Entry No. 1361026-83-6, which entered STN on Mar. 15, 2012.*
Alang et al. "Synthesis and antibacterial activity of some new benzothiazole derivatives", Acta Pharmaceutica Sciencia, 2010, vol. 52, p. 213-218, p. 215, compound R7.
International Search Report, issued in PCT/JP2012/061323, dated Jun. 5, 2012.
Khan et al. "Synthesis of 2,4,6-trichlorophenyl hydrazones and their inhibitory potential against glycation of protein", Medicinal Chemistry, 2011, 11.01, vol. 7, p. 572-580, p. 577, compound 8.
Motenegro et al. "Cytotoxic activity of polysubstituted 7-chloro-4-quinolinylhydrazone derivatives", Letters in Drug Design & Discovery, Mar. 15, 2012, vol. 9., p. 251-256, p. 252, compound 3d.
Ruffini, G. "Thin-layer chromatography of 2,4-dinitrophenylhydrazones of aromatic aldehydes and ketones", Journal of Chromatography, 1965, vol. 17, p. 483-487, p. 486, table III.
Sharma et al. "Computer aided drug design of 2-substituted hydrazino-6-fluoro-1,3-benzothiazoles as anti-microbial agents", Journal of Pharmacy Research, 2010, vol. 3, p. 969-970, p. 970, table 1, compound D3.
Siddiqui et al. "Cytotoxicity and enzymes estimation of some newer benzimidazoles", Annals of Biological Research, Dec. 29, 2011, vol. 2, p. 194-199, p. 197, compound 10.
Volmajer et al. "Synthesis of new iminocoumarins and their transformations into N-chloro and hydrazono compounds", Tetrahedron, 2005, vol. 61, p. 7012-7021, p. 7014, scheme 3, compound 18.
Xie et al. "Study on tumor chemotherapeutic agents: synthesis of 9-hydrazinoacridine derivatives", Yaoxue Xuebao, 1984, vol. 19, p. 466-470, p. 467, table 1, compounds 6, 12.
Cushman et al., "Synthesis and Evaluation of New Protein-Tyrosine Kinase Inhibitors. Part 2. Phenylhydrazones," Bioorganic & Medicinal Chemistry Letters, vol. 1, No. 4, 1991, pp. 215-218.
Extended European Search Report, dated Feb. 3, 2015, for European Application No. 12837151.5.
"CAS Registry Entry No. 860294-91-3," which entered STN on Aug. 15, 2005, 1 page.
Japanese Office Action, dated Jun. 28, 2016, for Japanese Application No. 2013-535962 with English language translation.

* cited by examiner

INTERMEDIATE FOR MANUFACTURE OF POLYMERIZABLE COMPOUND AND PROCESS FOR MANUFACTURE THEREOF

TECHNICAL FIELD

The invention relates to a novel compound that may be used as an intermediate for producing a polymerizable compound that may produce an optical film that achieves uniform conversion of polarized light over a wide wavelength band, and also relates to a method for producing the same.

BACKGROUND ART

A retardation film such as a quarter-wave plate that converts linearly polarized light into circularly polarized light, or a half-wave plate that converts the plane of vibration of linearly polarized light by 90°, has been widely used for a flat panel display and the like.

However, a known retardation film has a problem in that polarized light that passes through the retardation film is converted into colored polarized light. In order to solve the above problem, various wideband retardation films that can achieve uniform retardation for light over a wide wavelength band (i.e., retardation films having reverse wavelength dispersion) have been studied (see Patent Documents 1 to 6).

It has been desired to reduce the thickness of a flat panel display as much as possible along with an improvement in performance and widespread use of mobile information terminals (e.g., mobile personal computer and mobile phone). Therefore, a reduction in thickness of the retardation film has also been desired. It has been considered that the thickness of the retardation film can be most effectively reduced by producing the retardation film by applying a polymerizable composition that includes a low-molecular-weight polymerizable compound to a film substrate. Low-molecular-weight polymerizable compounds having excellent wavelength dispersion and polymerizable compositions using such polymerizable compounds have been proposed (see Patent Documents 7 to 24).

Patent Document 25 discloses a dihydroxy compound that has a structure similar to that of the compound according to the invention. However, Patent Document 25 does not disclose the compound according to the invention. Moreover, the compound disclosed in Patent Document 25 is used as a drug (i.e., enhancers of protein degradation).

RELATED-ART DOCUMENT

Patent Document

Patent Document 1: JP-A-10-68816
Patent Document 2: JP-A-10-90521
Patent Document 3: JP-A-11-52131
Patent Document 4: JP-A-2000-284126 (US20020159005A1)
Patent Document 5: JP-A-2001-4837
Patent Document 6: WO2000/026705
Patent Document 7: JP-A-2002-267838
Patent Document 8: JP-A-2003-160540 (US20030102458A1)
Patent Document 9: JP-A-2005-208414
Patent Document 10: JP-A-2005-208415
Patent Document 11: JP-A-2005-208416
Patent Document 12: JP-A-2005-289980 (US20070176145A1)
Patent Document 13: JP-A-2006-330710 (US20090072194A1)
Patent Document 14: JP-A-2009-179563 (US20090189120A1)
Patent Document 15: JP-A-2011-42606
Patent Document 16: JP-A-2010-31223
Patent Document 17: JP-A-2010-537954 (US20100201920A1)
Patent Document 18: JP-T-2010-537955 (US20100301271A1)
Patent Document 19: WO2006/052001 (US20070298191A1)
Patent Document 19: U.S. Pat. No. 6,139,771
Patent Document 20: U.S. Pat. No. 6,203,724
Patent Document 21: U.S. Pat. No. 5,567,349
Patent Document 22: JP-A-2011-6360
Patent Document 23: JP-A-2011-6361
Patent Document 24: WO2011/020883

SUMMARY OF THE INVENTION

Technical Problem

The inventors of the invention proposed a polymerizable compound that includes a partial structure represented by the following formula (A) in the molecule as a polymerizable compound that may produce an optical film that achieves uniform conversion of polarized light over a wide wavelength band (see Japanese Patent Application No. 2011-99525).

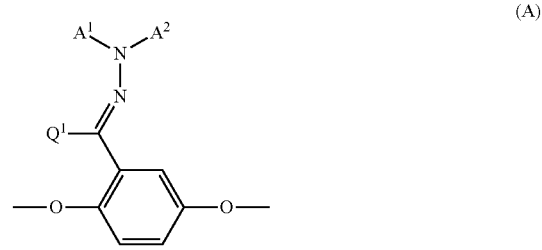

(A)

wherein $A^1$ is an organic group having 2 to 30 carbon atoms that includes at least one aromatic ring selected from the group consisting of an aromatic hydrocarbon ring and an aromatic hetero ring, $A^2$ is a hydrogen atom, a substituted or unsubstituted alkyl group having 1 to 6 carbon atoms, or an organic group having 2 to 30 carbon atoms that includes at least one aromatic ring selected from the group consisting of an aromatic hydrocarbon ring and an aromatic hetero ring, provided that the aromatic ring included in $A^1$ and $A^2$ is substituted or unsubstituted, and $A^1$ and $A^2$ optionally bond to form a ring, and $Q^1$ is a hydrogen atom, or a substituted or unsubstituted alkyl group having 1 to 6 carbon atoms.

An object of the invention is to provide a novel compound that may be used as an intermediate for producing the polymerizable compound disclosed in Japanese Patent Application No. 2011-99525, and a method for producing the same.

Solution to Problem

The inventors conducted extensive studies in order to achieve the above object. As a result, the inventors found that a novel compound represented by the following formula (I) is useful as an intermediate for producing the target polymerizable compound.

Several aspects of the invention provide the following compound (see (1) to (4)) and a method for producing the same (see (5) to (7)).

(1) A compound represented by the following formula (I),

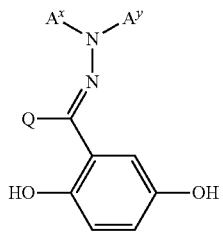

(I)

wherein $A^x$ is an organic group having 2 to 30 carbon atoms that includes at least one aromatic ring selected from the group consisting of an aromatic hydrocarbon ring and an aromatic hetero ring, $A^y$ is a hydrogen atom, a substituted or unsubstituted alkyl group having 1 to 18 carbon atoms, a substituted or unsubstituted cycloalkyl group, a substituted or unsubstituted alkenyl group having 2 to 18 carbon atoms, or an organic group having 2 to 30 carbon atoms that includes at least one aromatic ring selected from the group consisting of an aromatic hydrocarbon ring and an aromatic hetero ring, provided that the aromatic ring included in $A^x$ and $A^y$ is substituted or unsubstituted, and $A^x$ and $A^y$ optionally bond to each other to form a ring, and Q is a hydrogen atom, or a substituted or unsubstituted alkyl group having 1 to 6 carbon atoms.

(2) The compound according to (1), wherein the total number of aromatic ring π-electrons included in $A^x$ and $A^y$ is 24 or less.

(3) The compound according to (1) or (2), wherein Q is a hydrogen atom.

(4) The compound according to any one of (1) to (3), wherein $A^y$ is a hydrogen atom, or a substituted or unsubstituted alkyl group having 1 to 6 carbon atoms.

(5) A method for producing a hydrazone compound represented by a formula (I), the method including reacting a carbonyl compound represented by a formula (II) with a hydrazine compound represented by a formula (III) in a solvent,

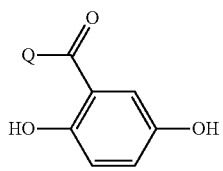

(II)

Q is a hydrogen atom, or a substituted or unsubstituted alkyl group having 1 to 6 carbon atoms,

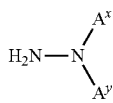

(III)

wherein $A^x$ is an organic group having 2 to 30 carbon atoms that includes at least one aromatic ring selected from the group consisting of an aromatic hydrocarbon ring and an aromatic hetero ring, $A^y$ is a hydrogen atom, a substituted or unsubstituted alkyl group having 1 to 18 carbon atoms, a substituted or unsubstituted cycloalkyl group, a substituted or unsubstituted alkenyl group having 2 to 18 carbon atoms, or an organic group having 2 to 30 carbon atoms that includes at least one aromatic ring selected from the group consisting of an aromatic hydrocarbon ring and an aromatic hetero ring, provided that the aromatic ring included in $A^x$ and $A^y$ is substituted or unsubstituted, and $A^x$ and $A^y$ optionally bond to each other to form a ring,

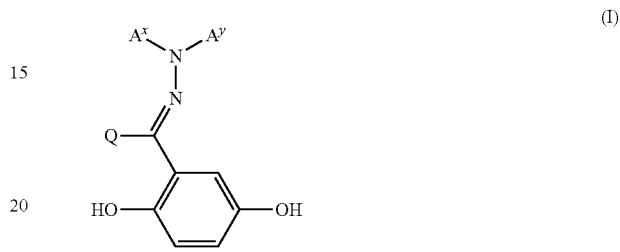

wherein Q, $A^x$, and $A^y$ are the same as defined above.

(6) The method according to (5), wherein the solvent is an alcohol-based solvent.

(7) The method according to (6), wherein the alcohol-based solvent is an alcohol-based solvent having 1 to 4 carbon atoms.

Advantageous Effects of the Invention

A polymerizable compound that makes it possible to produce an optical film that achieves uniform conversion of polarized light over a wide wavelength band can be inexpensively produced in high yield by utilizing the compound according to one aspect of the invention as an intermediate for producing the polymerizable compound.

The production method according to one aspect of the invention can advantageously produce the compound according to one aspect of the invention on an industrial scale.

A compound and a method for producing a compound according to several exemplary embodiments of the invention are described in detail below.

1) Compound

A compound according to one embodiment of the invention (hereinafter may be referred to as "compound (I)") is a novel compound represented by the formula (I).

$A^x$ in the formula (I) is an organic group having 2 to 30 carbon atoms that includes at least one aromatic ring selected from the group consisting of an aromatic hydrocarbon ring and an aromatic hetero ring.

The term "aromatic ring" used herein refers to a cyclic structure that exhibits aromaticity in a broad sense according to Huckel's rule (i.e., a cyclic conjugated structure that includes (4n+2) π-electrons, and a structure that exhibits aromaticity in which lone pairs of heteroatoms (e.g., sulfur, oxygen, or nitrogen) are involved in the π-electron system (e.g., thiophene, furan, and pyrrole)).

The organic group having 2 to 30 carbon atoms represented by $A^x$ that includes at least one aromatic ring selected from the group consisting of an aromatic hydrocarbon ring and an aromatic hetero ring, may include a plurality of aromatic rings, and may include both an aromatic hydrocarbon ring and an aromatic hetero ring.

Examples of the aromatic hydrocarbon ring include a benzene ring, a naphthalene ring, an anthracene ring, a fluorene ring, and the like. Examples of the aromatic hetero ring include 5-membered aromatic hetero rings such as a pyrrole ring, a furan ring, a thiophene ring, a pyrazole ring, an imidazole ring, an oxazole ring, and a thiazole ring; 6-membered aromatic hetero rings such as a pyridine ring, a pyridazine ring, a pyrimidine ring, and a pyrazine ring; fused aromatic hetero rings such as a benzimidazole ring, a benzothiophene ring, a benzofuran ring, a benzothiazole ring, a benzoxazole ring, a quinoline ring, a phthalazine ring, and a carbazole ring; and the like.

The aromatic ring included in $A^x$ may be substituted with a substituent. Examples of the substituent include halogen atoms such as a fluorine atom and a chlorine atom; a cyano group; alkyl groups having 1 to 6 carbon atoms such as a methyl group, an ethyl group, and a propyl group; alkenyl groups having 2 to 6 carbon atoms such as a vinyl group and an allyl group; alkyl halide groups having 1 to 6 carbon atoms such as a trifluoromethyl group; substituted amino groups such as a dimethylamino group; alkoxy groups having 1 to 6 carbon atoms such as a methoxy group, an ethoxy group, and an isopropoxy group; a nitro group; aryl groups such as a phenyl group and a naphthyl group; a —C(=O)—OR group; an —SO$_2$R group; and the like. R is an alkyl group having 1 to 6 carbon atoms (e.g., methyl group or ethyl group) or an aryl group having 6 to 14 carbon atoms (e.g., phenyl group or naphthyl group).

The aromatic ring included in $A^x$ may be substituted with a plurality of identical or different substituents, and two adjacent substituents may bond to each other to form a ring. A ring formed by two adjacent substituents may be a monocyclic ring, or may be a fused polycyclic ring.

Note that the number of carbon atoms (i.e., 2 to 30) of the organic group represented by $A^x$ refers to the total number of carbon atoms of the organic group that includes an aromatic ring, excluding the number of carbon atoms of a substituent. This also applies to the number of carbon atoms of the organic group represented by $A^y$.

Examples of the organic group having 2 to 30 carbon atoms represented by $A^x$ that includes at least one aromatic ring selected from the group consisting of an aromatic hydrocarbon ring and an aromatic hetero ring, include aromatic cyclic hydrocarbon groups; aromatic heterocyclic groups; alkyl groups having 3 to 30 carbon atoms that include at least one aromatic ring selected from the group consisting of an aromatic hydrocarbon ring and an aromatic hetero ring; alkenyl groups having 4 to 30 carbon atoms that include at least one aromatic ring selected from the group consisting of an aromatic hydrocarbon ring and an aromatic hetero ring; alkynyl groups having 4 to 30 carbon atoms that include at least one aromatic ring selected from the group consisting of an aromatic hydrocarbon ring and an aromatic hetero ring; and the like.

Among these, aromatic groups (aromatic cyclic hydrocarbon groups or aromatic heterocyclic groups) are preferable as $A^x$.

$A^y$ is a hydrogen atom, a substituted or unsubstituted alkyl group having 1 to 18 carbon atoms, a substituted or unsubstituted cycloalkyl group, a substituted or unsubstituted alkenyl group having 2 to 18 carbon atoms, or an organic group having 2 to 30 carbon atoms that includes at least one aromatic ring selected from the group consisting of an aromatic hydrocarbon ring and an aromatic hetero ring.

Examples of the alkyl group having 1 to 18 carbon atoms represented by $A^y$ include a methyl group, an ethyl group, an n-propyl group, an isopropyl group, an n-butyl group, a sec-butyl group, a t-butyl group, an n-pentyl group, an isopentyl group, an n-hexyl group, an isohexyl group, an n-heptyl group, an isohexyl group, an n-octyl group, an n-decyl group, an n-undecyl group, an n-dodecyl group, an n-tetradecyl group, an n-pentadecyl group, an n-hexadecyl group, an n-octadecyl group, and the like.

Examples of a substituent that may substitute the substituted or unsubstituted alkyl group having 1 to 18 carbon atoms include halogen atoms such as a fluorine atom and a chlorine atom; a cyano group; substituted amino groups such as a dimethylamino group; alkoxy groups having 1 to 6 carbon atoms such as a methoxy group, an ethoxy group, and an isopropoxy group; a nitro group; cycloalkyl groups having 3 to 8 carbon atoms such as a cyclopropyl group and a cyclohexyl group; aryl groups such as a phenyl group and a naphthyl group; a —C(=O)—OR group; an —SO$_2$R group; and the like. Note that R is the same as defined above.

Examples of the unsubstituted cycloalkyl group include cycloalkyl groups having 3 to 12 carbon atoms (e.g., cyclopropyl group, cyclobutyl group, cyclopentyl group, cyclohexyl group, cyclo heptyl group, and cyclooctyl group).

Examples of a substituent that may substitute the substituted or unsubstituted cycloalkyl group include halogen atoms such as a fluorine atom and a chlorine atom; a cyano group; substituted amino groups such as a dimethylamino group; alkoxy groups having 1 to 6 carbon atoms such as a methoxy group, an ethoxy group, and an isopropoxy group; a nitro group; alkyl groups having 3 to 8 carbon atoms such as a methyl group, an ethyl group, an isopropyl group, and a t-butyl group; aryl groups such as a phenyl group and a naphthyl group; a —C(=O)—OR group; an —SO$_2$R group; and the like. Note that R is the same as defined above.

Examples of the substituted or unsubstituted alkenyl group having 2 to 18 carbon atoms include a vinyl group, a 1-propenyl group, an allyl group, a 1-butenyl group, a 2-butenyl group, a 3-butenyl group, a pentenyl group, a hexenyl group, a heptenyl group, and the like.

Examples of a substituent that may substitute the substituted or unsubstituted alkenyl group having 2 to 18 carbon atoms include those mentioned above in connection with the substituted or unsubstituted alkyl group having 1 to 18 carbon atoms.

Examples of the organic group having 2 to 30 carbon atoms represented by $A^y$ that includes at least one aromatic ring selected from the group consisting of an aromatic hydrocarbon ring and an aromatic hetero ring, include those mentioned above in connection with $A^x$.

The aromatic ring included in $A^y$ may be substituted with a substituent at an arbitrary position. Examples of the substituent include those mentioned above in connection with a substituent that may substitute the aromatic ring included in $A^x$.

$A^y$ is preferably a hydrogen atom, a substituted or unsubstituted alkyl group having 1 to 6 carbon atoms, a cycloalkyl group having 3 to 8 carbon atoms, or an alkenyl group having 2 to 8 carbon atoms, and more preferably a hydrogen atom, or a substituted or unsubstituted alkyl group having 1 to 6 carbon atoms.

Specific examples of the aromatic ring that may be included in $A^x$ and $A^y$ are shown below. Note that the aromatic ring that may be included in $A^x$ and $A^y$ is not limited thereto. Note also that the aromatic ring is bonded to the nitrogen atom through the bond indicated by "-".

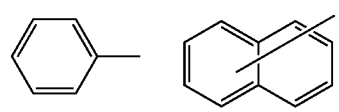

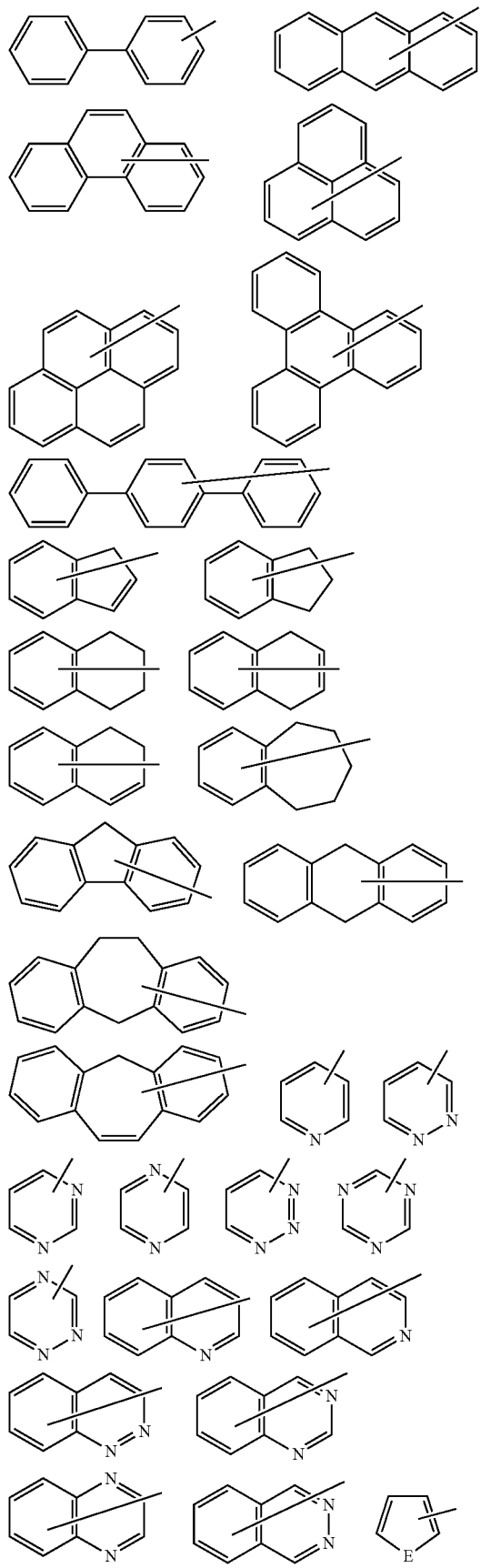
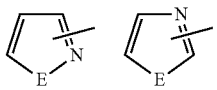
wherein E is NR³, an oxygen atom, or a sulfur atom, and R³ is a hydrogen atom, or an alkyl group having 1 to 6 carbon atoms (e.g., methyl group or ethyl group).

-continued

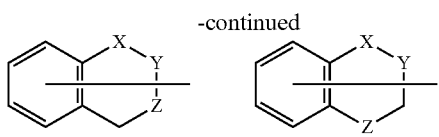

wherein X, Y, and Z are independently NR³, an oxygen atom, a sulfur atom, —SO—, or —SO₂—, provided that a case where two or more oxygen atoms, sulfur atoms, —SO—, or —SO₂— are situated at adjacent positions is excluded, and R³ is the same as defined above.

Among these, the following aromatic rings are preferable.

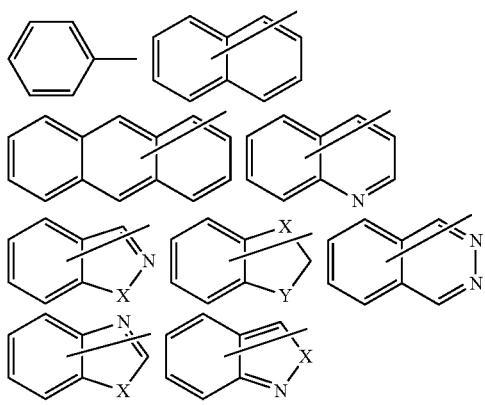

Among these, the following aromatic rings are more preferable.

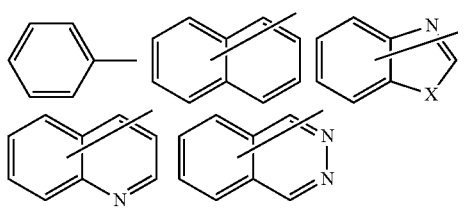

Among these, the following aromatic rings are particularly preferable.

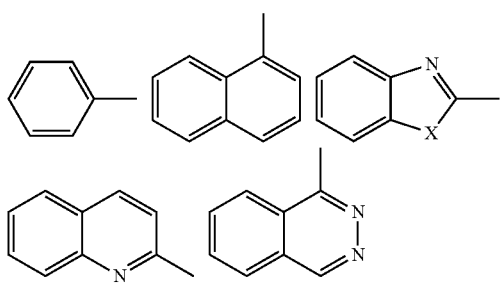

wherein X and Y are the same as defined above.

A$^x$ and A$^y$ optionally bond to each other to form a ring. Examples of the ring formed by A$^x$ and A$^y$ include a substituted or unsubstituted unsaturated hetero ring having 4 to 30 carbon atoms, and a substituted or unsubstituted unsaturated carbon ring having 6 to 30 carbon atoms.

The unsaturated hetero ring having 4 to 30 carbon atoms and the unsaturated carbon ring having 6 to 30 carbon atoms may or may not exhibit aromaticity. Examples of the unsaturated hetero ring having 4 to 30 carbon atoms and the unsaturated carbon ring having 6 to 30 carbon atoms are shown below.

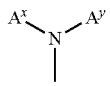

Note that the following rings indicate the above part in the formula (I).

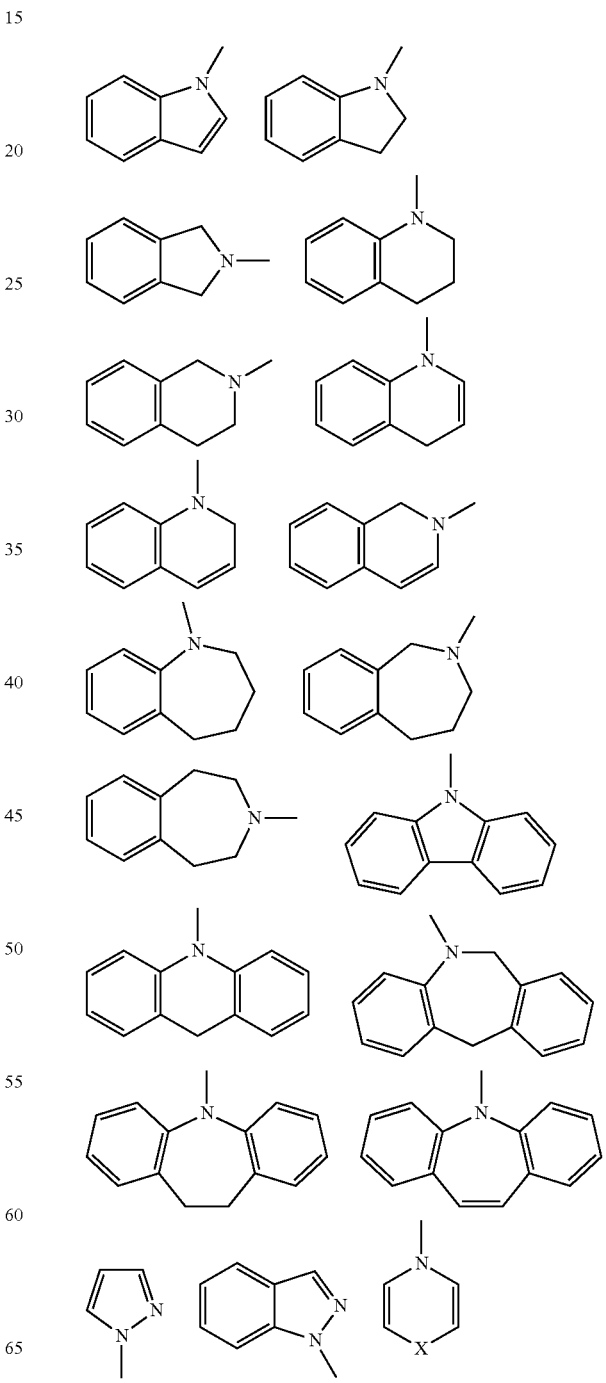

-continued

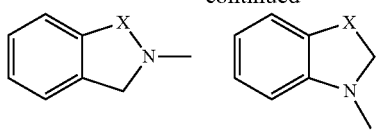
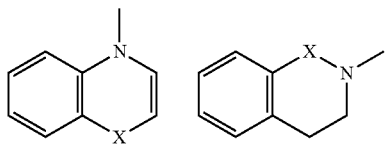
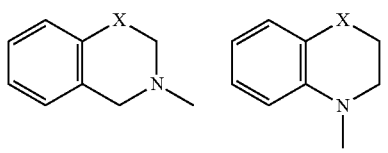
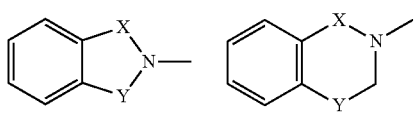
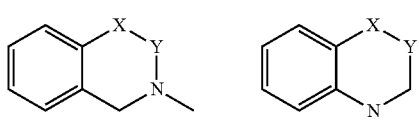
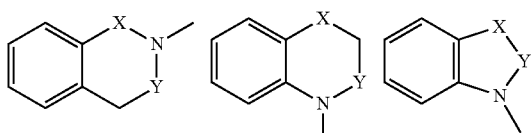
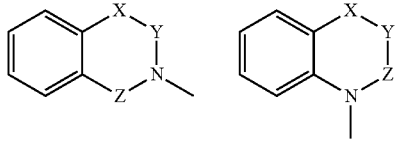
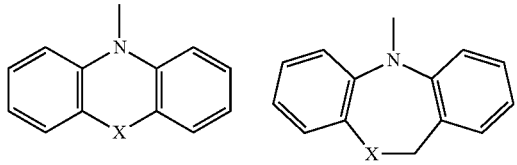
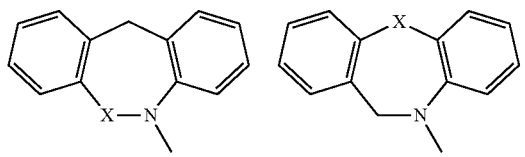
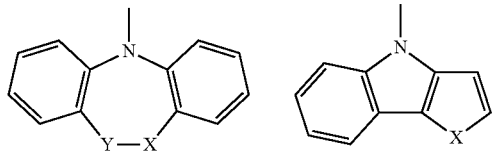
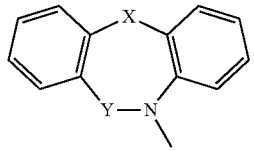

-continued

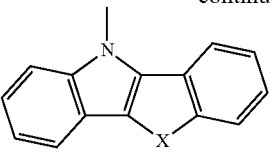

wherein X, Y, and Z are the same as defined above.

The above rings may be substituted with a substituent.

Examples of the substituent include halogen atoms, a cyano group, alkyl groups having 1 to 6 carbon atoms, alkoxy groups having 1 to 6 carbon atoms, a nitro group, a —C(=O)—OR group, an —SO$_2$R group, and the like. Note that R is the same as defined above.

The total number of π-electrons included in $A^x$ and $A^y$ is preferably 24 or less, more preferably 4 to 24, and still more preferably 6 to 18, in order to ensure that a preferable intermediate for producing a polymerizable compound is obtained.

It is preferable that $A^x$ be an aromatic group having 4 to 30 carbon atoms, and $A^y$ be a hydrogen atom, a substituted or unsubstituted alkyl group having 1 to 6 carbon atoms, a cycloalkyl group having 3 to 8 carbon atoms, or a substituted or unsubstituted alkenyl group having 2 to 8 carbon atoms, or $A^x$ and $A^y$ bond to each other to form an unsaturated hetero ring or an unsaturated carbon ring, and it is particularly preferable that $A^x$ be an aromatic group having 4 to 30 carbon atoms, and $A^y$ be a hydrogen atom, a substituted or unsubstituted alkyl group having 1 to 6 carbon atoms, a cycloalkyl group having 3 to 8 carbon atoms, or a substituted or unsubstituted alkenyl group having 2 to 8 carbon atoms, in order to ensure that a preferable intermediate for producing a polymerizable compound is obtained.

Q is a hydrogen atom, or a substituted or unsubstituted alkyl group having 1 to 6 carbon atoms.

Examples of the substituted or unsubstituted alkyl group having 1 to 6 carbon atoms include those mentioned above in connection with $A^y$.

Q is preferably a hydrogen atom or an alkyl group having 1 to 6 carbon atoms, and more preferably a hydrogen atom.

The compound according to one embodiment of the invention may be useful as an intermediate for producing a polymerizable compound that may produce an optical film that achieves uniform conversion of polarized light over a wide wavelength band. Examples of the polymerizable compound produced using the compound according to one embodiment of the invention as an intermediate include the compounds disclosed in JP-A-2011-099525, the compounds described in the examples, and the like.

These compounds may produce an optical film that achieves uniform conversion of polarized light over a wide wavelength band, have a practical low melting point, exhibit excellent solubility in a general-purpose solvent, and can be produced at low cost.

The compound according to one embodiment of the invention may be produced by an arbitrary method. For example, the compound according to one embodiment of the invention can be conveniently produced in high yield using the following production method.

2) Method for Producing Compound

A method for producing a hydrazone compound represented by the formula (I) (compound (I)) according to one embodiment of the invention includes reacting a carbonyl compound represented by the formula (II) (hereinafter may be referred to as "carbonyl compound (II)") with a hydrazine compound represented by the formula (III) (hereinafter may be referred to as "hydrazine compound (III)") in a solvent. Note that $A^x$, $A^y$, and Q in the formulas (I), (II), and (III) are the same as defined above.

Examples of the solvent include alcohol-based solvents, ether-based solvents, and the like.

Examples of the ether-based solvents include ethers such as diethyl ether, tetrahydrofuran, 1,2-dimethoxyethane, 1,4-dioxane, and cyclopentyl methyl ether, and the like.

Examples of the alcohol-based solvents include methyl alcohol, ethyl alcohol, n-propyl alcohol, isopropyl alcohol, n-butyl alcohol, isobutyl alcohol, sec-butyl alcohol, tert-butyl alcohol, n-pentyl alcohol, amyl alcohol, and the like.

It is preferable to use an alcohol-based solvent (more preferably an alcohol having 1 to 4 carbon atoms) as the reaction solvent since the target product can be obtained in higher yield, and can be more easily isolated.

These alcohols (alcohol-based solvents) may be used either alone or in combination.

The alcohol-based solvents may be used in combination with an additional solvent. Examples of the additional solvent include ether-based solvents such as tetrahydrofuran, and the like.

The solvent may be used in an appropriate amount taking account of the type of each compound, the reaction scale, and the like, but is normally used in an amount of 1 to 100 ml per gram of the hydrazine compound (III).

The carbonyl compound (II) and the hydrazine compound (III) are normally used in a molar ratio (carbonyl compound (II):hydrazine compound (III)) of 1:2 to 2:1, and preferably 1:1.5 to 1.5:1.

The above reaction may be effected in the presence of an acid catalyst such as an organic acid (e.g., (±)-10-camphorsulfonic acid or p-toluenesulfonic acid), a salt thereof, or an inorganic acid (e.g., hydrochloric acid or sulfuric acid). The addition of the acid catalyst may reduce the reaction time, and improve the yield. The acid catalyst is normally added in an amount of 0.001 to 1 mol based on 1 mol of the carbonyl compound (II). The acid catalyst may be added directly, or may be added in the form of a solution prepared by dissolving the acid catalyst in an appropriate solvent.

The reaction proceeds smoothly when the reaction temperature is within the range from −10° C. to the boiling point of the solvent. The reaction time is determined taking account of the reaction scale, and is normally several minutes to several tens of hours, and preferably 30 minutes to 10 hours.

The target product may be isolated by performing a post-treatment operation normally employed in organic chemistry after completion of the reaction, optionally followed by a known purification/separation means such as column chromatography, recrystallization, or distillation. The compound according to one embodiment of the invention can be obtained in high yield using the above production method.

The structure of the target product may be identified by measurement (e.g., NMR spectrometry, IR spectrometry, or mass spectrometry), elemental analysis, or the like.

The hydrazine compound (III) may be produced as described below.

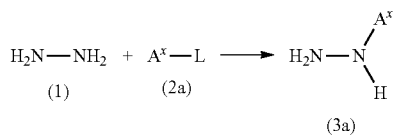

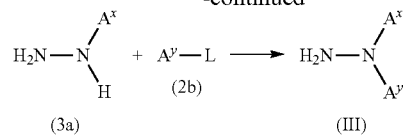

wherein $A^x$ and $A^y$ are the same as defined above, and L is a leaving group (e.g., halogen atom, methanesulfonyloxy group, or p-toluenesulfonyloxy group).

Specifically, a compound represented by the formula (2a) is reacted with hydrazine (1) in an appropriate solvent in a molar ratio (compound (2a):hydrazine (1)) of 1:1 to 1:20 (preferably 1:2 to 1:10) to obtain the corresponding hydrazine compound (3a), and the hydrazine compound (3a) is reacted with a compound represented by the formula (2b) to obtain the hydrazine compound (III).

Hydrazine monohydrate is normally used as the hydrazine (1). A commercially available product may be used directly as the hydrazine (1).

The solvent used for the above reaction is not particularly limited as long as the solvent is inert to the reaction. Examples of the solvent include alcohols such as methyl alcohol, ethyl alcohol, n-propyl alcohol, isopropyl alcohol, n-butyl alcohol, isobutyl alcohol, sec-butyl alcohol, tert-butyl alcohol, n-pentyl alcohol, and amyl alcohol; ethers such as diethyl ether, tetrahydrofuran, 1,2-dimethoxyethane, 1,4-dioxane, and cyclopentyl methyl ether; aromatic hydrocarbons such as benzene, toluene, and xylene; aliphatic hydrocarbons such as n-pentane, n-hexane, and n-heptane; amides such as N,N-dimethylformamide, N-methylpyrrolidone, and hexamethylphosphoric triamide; sulfur-containing solvents such as dimethyl sulfoxide and sulfolane; mixed solvents including two or more of these compounds; and the like.

Among these, alcohols, ethers, and mixed solvents of an alcohol and an ether are preferable.

The solvent may be used in an appropriate amount taking account of the type of each compound, the reaction scale, and the like, but is normally used in an amount of 1 to 100 ml per gram of hydrazine.

The reaction proceeds smoothly when the reaction temperature is within the range from −10° C. to the boiling point of the solvent. The reaction time is determined taking account of the reaction scale, but is normally several minutes to several hours.

The hydrazine compound (III) may also be produced by reducing a diazonium salt (4) (see below) using a known method.

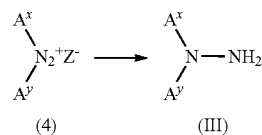

wherein $A^x$ and $A^y$ are the same as defined above, and $Z^-$ is an anion that is a counter ion for diazonium. Examples of the anion represented by $Z^-$ include inorganic anions such as a hexafluorophosphoric acid ion, a fluoroboric acid ion, a chloride ion, and a sulfuric acid ion; organic anions such as a polyfluoroalkylcarboxylic acid ion, a polyfluoroalkylsulfonic acid ion, a tetraphenylboric acid ion, an aromatic carboxylic acid ion, and an aromatic sulfonic acid ion; and the like.

Examples of a reducing agent used for the above reaction include a metal salt reducing agent and the like.

The term "metal salt reducing agent" normally refers to a compound that includes a metal having a small valence, or a compound that includes a metal ion and a hydrido source (see "*Yuki Gosei Jikkenhou Handbook* (Handbook of Organic Synthesis Experiments)", 1990, edited by The Society of Synthetic Organic Chemistry, Japan, published by Maruzen Co., Ltd., p. 810).

Examples of the metal salt reducing agent include $NaAlH_4$, $NaAlH_p(Or)_q$ (wherein p is an integer from 1 to 3, q is an integer that satisfies p+q=4, and r is an alkyl group), $LiAlH_4$, $iBu_2AlH$, $LiBH_4$, $NaBH_4$, $SnCl_2$, $CrCl_2$, $TiCl_3$, and the like.

The reduction reaction may be effected under known reaction conditions. For example, the reduction reaction may be effected under the reaction conditions described in JP-A-2005-336103, "*Shin-Jikken Kagaku Koza* (New Experimental Chemistry Course)", 1978, Vol. 14, published by Maruzen Co., Ltd., "*Jikken Kagaku Koza* (Experimental Chemistry Course)", 1992, Vol. 20, published by Maruzen Co., Ltd., or the like.

The diazonium salt (4) may be produced from aniline or the like using a known method.

According to the above production method, the compound according to one embodiment of the invention can be conveniently produced in high yield, and the target polymerizable compound can be conveniently produced at low cost.

EXAMPLES

The invention is further described below by way of examples. Note that the invention is not limited to the following examples and the like.

Example 1a

Production of Compound (I-1)

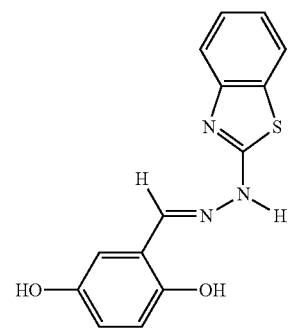

Compound (I-1)

A four-necked reactor equipped with a thermometer was charged with 5.6 g (40.5 mmol) of 2,5-dihydroxybenzaldehyde, 6.9 g (41.8 mmol) of 2-hydrazinobenzothiazole, and 200 ml of methanol under a nitrogen stream. The mixture was refluxed for 1 hour with heating. After completion of the reaction, the reaction mixture was cooled to 20° C. to precipitate a solid, which was filtered off. The solid collected by filtration was washed with methanol, and dried using a vacuum dryer to obtain 10.6 g of a compound (I-1) as a light yellow solid (yield: 91.7%).

The structure of the target product was identified by $^1$H-NMR.

The $^1$H-NMR spectrum data are shown below.

$^1$H-NMR (500 MHz, DMSO-$d_6$, TMS, δ ppm): 12.18 (s, 1H), 9.72 (s, 1H), 9.00 (s, 1H), 8.41 (s, 1H), 7.77 (d, 1H, J=7.5 Hz), 7.41 (d, 1H, J=8.0 Hz), 7.28 (ddd, 1H, J=1.0 Hz, 8.0 Hz, 8.0 Hz), 7.13-7.10 (m, 2H), 6.78 (d, 1H, J=8.5 Hz), 6.73 (d, 1H, J=3.0 Hz, 8.5 Hz)

Example 1b

Production of Compound (I-1)

A compound was produced in the same manner as in Example 1a, except that 1-propanol was used instead of methanol as the solvent used for the reaction and the post-treatment. 10.7 g of a compound (I-1) was thus obtained as a light yellow solid (yield: 92.5%).

Example 1c

Production of Compound (I-1)

The same operations as those of Example 1a were performed, except that tetrahydrofuran (THF) was used as the reaction solvent instead of methanol. After completion of the reaction, a solid precipitate was not observed, and THF was evaporated under reduced pressure using a rotary evaporator to obtain a yellow solid. The yellow solid was purified by silica gel column chromatography (chloroform:methanol=85:15 (volume ratio)) to obtain 8.78 g of a compound (I-1) as a light yellow solid (yield: 75.9%).

Example 2a

Production of Compound (I-2)

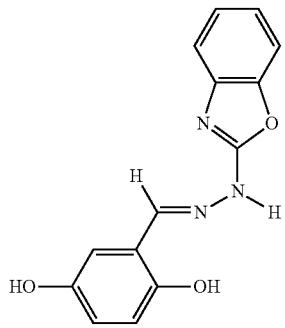

Compound (I-2)

Step 1: Synthesis of Raw Material A

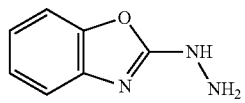

Raw material A

A four-necked reactor equipped with a thermometer was charged with 49 g (0.98 mol) of hydrazine monohydrate and 500 ml of ethanol under a nitrogen stream to prepare a homogeneous solution. The solution was heated to 50° C. After the addition of 30 g (0.20 mmol) of 2-chlorobenzoxazole dissolved in 250 ml of ethanol, the mixture was stirred at 50° C. for 1 hour. After completion of the reaction, the reaction mixture was added to 1.5 l of 10% sodium bicarbonate water, and extracted twice with 500 ml of chloroform. The chloroform layer was collected, washed with 800 ml of 10% sodium bicarbonate water, and dried over anhydrous sodium sulfate, and sodium sulfate was filtered off. Chloroform was evaporated from the filtrate under reduced pressure using a rotary evaporator to obtain 18 g of a raw material A as a white solid. The white solid was used directly for a step 2 without purification.

Step 2: Synthesis of Compound (I-2)

A four-necked reactor equipped with a thermometer was charged with 5.4 g (39.1 mmol) of 2,5-dihydroxybenzaldehyde, 5.83 g (39.1 mmol) of the raw material A, and 150 ml of ethanol under a nitrogen stream. The mixture was stirred at 25° C. for 4 hours. After completion of the reaction, a solid precipitate was filtered off. The solid collected by filtration was washed with ethanol, and dried using a vacuum dryer to obtain 10.1 g of a compound (I-2) as a white solid (yield: 95.9%).

The structure of the target product was identified by $^1$H-NMR.

The $^1$H-NMR spectrum data are shown below.

$^1$H-NMR (500 MHz, DMSO-$d_6$, TMS, δ ppm): 12.1 (s, 1H), 9.81 (brs, 1H), 8.98 (s, 1H), 8.39 (s, 1H), 7.52 (d, 1H, J=8.0 Hz), 7.40 (d, 1H, J=7.5 Hz), 7.22 (dd, 1H, J=7.5 Hz, 7.5 Hz), 7.13-7.10 (m, 2H), 6.76 (d, 1H, J=8.5 Hz), 6.71 (dd, 1H, J=2.5 Hz, 8.5 Hz)

Example 2b

Synthesis of Compound (I-2)

The same operations as those of the step 2 of Example 2a were performed, except that THF was used as the reaction solvent instead of ethanol. After completion of the reaction, a solid precipitate was not observed, and THF was evaporated under reduced pressure using a rotary evaporator to obtain a light yellow solid. The light yellow solid was purified by silica gel column chromatography (chloroform:methanol=85:15 (volume ratio)) to obtain 8.69 g of a compound (I-2) as a white solid (yield: 82.5%).

Example 3

Synthesis of Compound (I-3)

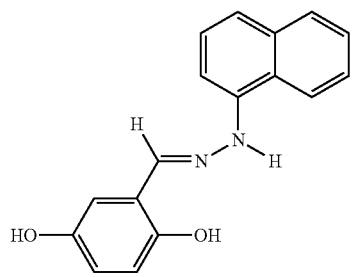

Compound (I-3)

A four-necked reactor equipped with a thermometer was charged with 5.4 g (39.1 mmol) of 2,5-dihydroxybenzaldehyde, 7.6 g (39.1 mmol) of 1-naphthylhydrazine hydrochloride, and 100 ml of methanol under a nitrogen stream to prepare a homogenous solution. After the addition of 182 mg (0.78 mmol) of (±)-10-camphorsulfonic acid to the solution, the mixture was stirred at 25° C. for 2 hours. After completion of the reaction, a solid precipitate was filtered off. The solid collected by filtration was washed with methanol, and dried using a vacuum dryer to obtain 7.8 g of a compound (I-3) as an orange solid (yield: 71.7%).

The structure of the target product was identified by $^1$H-NMR.

The $^1$H-NMR spectrum data are shown below.

$^1$H-NMR (500 MHz, DMSO-$d_6$, TMS, δ ppm): 10.54 (s, 1H), 9.82 (s, 1H), 8.83 (s, 1H), 8.47 (s, 1H), 8.50-8.37 (brs, 1H), 8.31 (d, 1H, J=8.0 Hz), 7.87 (d, 1H, J=8.5 Hz), 7.50-7.41 (m, 2H), 7.13 (d, 1H, J=8.5 Hz), 6.98 (d, 1H, J=2.5 Hz), 6.84 (d, 1H, J=8.0 Hz), 6.70 (d, 1H, J=8.5 Hz), 6.61 (dd, 1H, J=3.0 Hz, 8.5 Hz)

Example 4

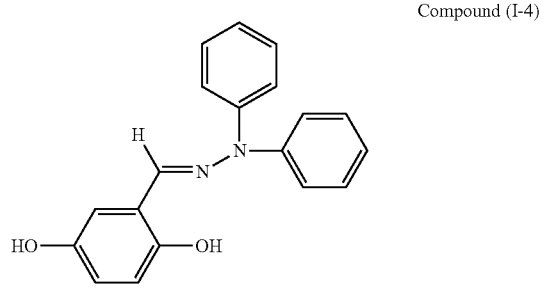 [SMILES: Oc1ccc(O)c(/C=N/N(c2ccccc2)c2ccccc2)c1]

Compound (I-4)

A four-necked reactor equipped with a thermometer was charged with 5.4 g (39.1 mmol) of 2,5-dihydroxybenzaldehyde, 7.2 g (39.1 mmol) of N,N-diphenylhydrazine, and 100 ml of ethanol under a nitrogen stream. The mixture was stirred at 25° C. for 3 hours. After completion of the reaction, a solid precipitate was filtered off. The solid collected by filtration was washed with ethanol, and dried using a vacuum dryer to obtain 9.8 g of a compound (I-4) as a light brown solid (yield: 82.4%).

The structure of the target product was identified by $^1$H-NMR.

The $^1$H-NMR spectrum data are shown below.

$^1$H-NMR (500 MHz, DMSO-$d_6$, TMS, δ ppm): 9.30 (s, 1H), 8.83 (s, 1H), 7.49-7.45 (m, 4H), 7.39 (s, 1H), 7.23-7.20 (m, 2H), 7.15-7.13 (m, 5H), 6.66 (d, 1H, J=8.5 Hz), 6.58 (dd, 1H, J=3.0 Hz, 8.5 Hz)

Example 5a

Synthesis of Compound (I-5)

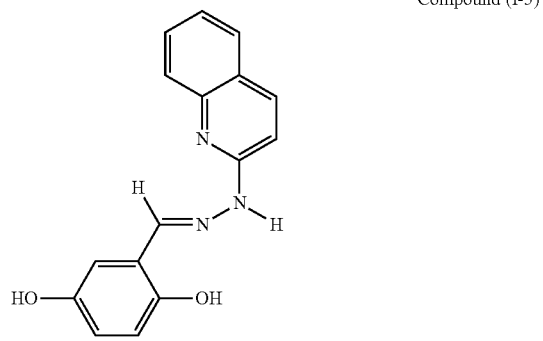

Compound (I-5)

A four-necked reactor equipped with a thermometer was charged with 5.4 g (39.1 mmol) of 2,5-dihydroxybenzaldehyde, 6.2 g (39.1 mmol) of 2-hydrazinoquinoline, and 200 ml of ethanol under a nitrogen stream. The mixture was stirred at 25° C. for 6 hours. After completion of the reaction, a solid precipitate was filtered off. The solid collected by filtration was washed with ethanol, and dried using a vacuum dryer to obtain 9.9 g of a compound (I-5) as a light yellow solid (yield: 90.7%).

The structure of the target product was identified by $^1$H-NMR.

The $^1$H-NMR spectrum data are shown below.

$^1$H-NMR (500 MHz, DMSO-$d_6$, TMS, δ ppm): 11.33 (s, 1H), 9.74 (s, 1H), 8.89 (s, 1H), 8.31 (s, 1H), 8.19 (d, 1H, J=8.5 Hz), 7.78 (d, 1H, J=7.5 Hz), 7.64-7.58 (m, 2H), 7.43 (d, 1H, J=8.5 Hz), 7.29 (dd, 1H, J=7.5 Hz, 7.5 Hz), 7.11 (d, 1H, J=3.0 Hz), 6.74 (d, 1H, J=8.5 Hz), 6.66 (dd, 1H, J=3.0 Hz, 8.5 Hz)

Example 5b

Synthesis of Compound (I-5)

The same operations as those of Example 5a were performed, except that THF was used as the reaction solvent instead of ethanol. After completion of the reaction, a solid precipitate was not observed, and THF was evaporated under reduced pressure using a rotary evaporator to obtain a yellow solid. The yellow solid was purified by silica gel column chromatography (chloroform:methanol=85:15 (volume ratio)) to obtain 7.70 g of a compound (I-5) as a yellow solid (yield: 70.5%).

Example 6

Production of Compound (I-6)

Compound (I-6)

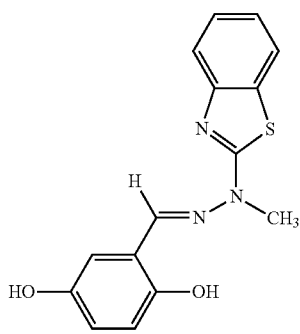

Step 1: Synthesis of Raw Material B

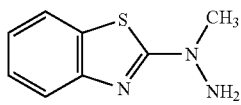

Raw material B

A four-necked reactor equipped with a thermometer was charged with 1.00 g (6.05 mmol) of 2-hydrazinobenzothiazole and 15 ml of THF under a nitrogen stream to prepare a homogeneous solution. 4.5 ml (7.26 mmol) of lithium hexamethyldisilazane (26% THF solution) was slowly added dropwise to the solution at 0° C. The mixture was stirred at 0° C. for 30 minutes. After the addition of 0.46 ml (7.26 mmol) of methyl iodide, the mixture was stirred at 25° C. for 3 hours. After completion of the reaction, the reaction mixture was added to 100 ml of water, and extracted with 100 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=70:30 (volume ratio)) to obtain 693 mg of a raw material B as a light yellow solid (yield: 63.9%).

The structure of the target product was identified by $^1$H-NMR.

The $^1$H-NMR spectrum data are shown below.

$^1$H-NMR (500 MHz, CDCl$_3$, TMS, δ ppm): 7.61 (dd, 1H, J=1.0 Hz, 8.0 Hz), 7.55 (dd, 1H, J=1.0 Hz, 7.5 Hz), 7.29 (ddd, 1H, J=1.0 Hz, 7.5 Hz, 8.0 Hz), 7.08 (ddd, 1H, J=1.0 Hz, 7.5 Hz, 7.5 Hz), 4.31 (s, 2H), 3.45 (s, 3H)

Step 2: Synthesis of Compound (I-6)

A four-necked reactor equipped with a thermometer was charged with 380 mg (2.75 mmol) of 2,5-dihydroxybenzaldehyde, 493 mg (2.75 mmol) of the raw material B, and 10 ml of 1-propanol under a nitrogen stream. The mixture was stirred at 80° C. for 1 hour. After completion of the reaction, the reaction mixture was cooled to 20° C. to precipitate a solid, which was filtered off. The solid collected by filtration was washed with 1-propanol, and dried using a vacuum dryer to obtain 599 mg of a compound (I-6) as a light yellow solid (yield: 72.7%).

The structure of the target product was identified by $^1$H-NMR.

The $^1$H-NMR spectrum data are shown below.

$^1$H-NMR (400 MHz, DMSO-$d_6$, TMS, δ ppm): 9.42 (s, 1H), 8.97 (s, 1H), 8.08 (s, 1H), 7.84 (dd, 1H, J=1.0 Hz, 8.0 Hz), 7.60 (dd, 1H, J=1.0 Hz, 8.0 Hz), 7.38 (ddd, 1H, J=1.0, 7.5, 8.0 Hz), 7.19 (d, 1H, J=3.0 Hz), 7.16 (ddd, 1H, J=1.0 Hz, 7.5 Hz, 8.0 Hz), 6.77 (d, 1H, J=9.0 Hz), 6.70 (dd, 1H, J=9.0 Hz), 3.70 (s, 3H)

Example 7

Synthesis of Compound (I-7)

Compound (I-7)

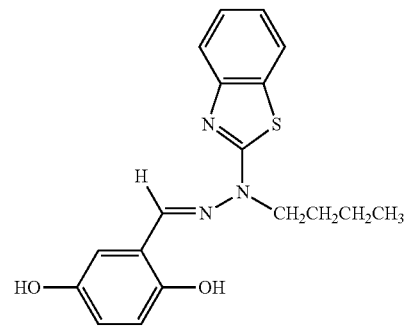

Step 1: Synthesis of Raw Material C

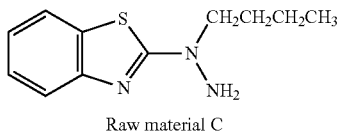
Raw material C

Example 8

Synthesis of Compound (I-8)

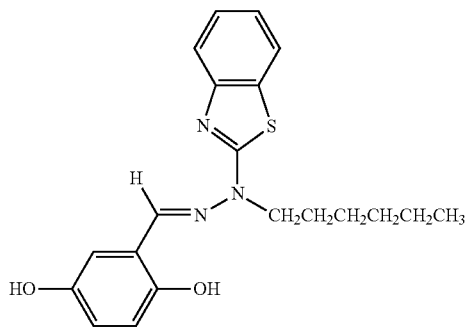
Compound (I-8)

Step 1: Synthesis of Raw Material D

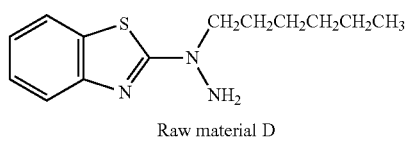
Raw material D

A four-necked reactor equipped with a thermometer was charged with 2.00 g (12.1 mmol) of 2-hydrazinobenzothiazole and 20 ml of N,N-dimethylformamide (DMF) under a nitrogen stream to prepare a homogeneous solution. After the addition of 8.36 g (60.5 mmol) of potassium carbonate and 2.67 g (14.5 mmol) of 1-iodobutane to the solution, the mixture was stirred at 50° C. for 7 hours. After completion of the reaction, the reaction mixture was cooled to 20° C., added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio)) to obtain 2.34 g of a raw material C as a white solid (yield: 87.4%).

The structure of the target product was identified by $^1$H-NMR.

The $^1$H-NMR spectrum data are shown below.

$^1$H-NMR (400 MHz, CDCl$_3$, TMS, δ ppm): 7.59 (d, 1H, J=7.8 Hz), 7.52 (d, 1H, J=7.8 Hz), 7.27 (dd, 1H, J=7.3 Hz, 7.8 Hz), 7.05 (dd, 1H, J=7.3 Hz, 7.8 Hz), 4.21 (s, 2H), 3.75 (t, 2H, J=7.3 Hz), 1.68-1.75 (m, 2H), 1.37-1.46 (m, 2H), 0.97 (t, 3H, J=7.3 Hz)

Step 2: Synthesis of Compound (I-7)

A four-necked reactor equipped with a thermometer was charged with 763 mg (5.52 mmol) of 2,5-dihydroxybenzaldehyde, 1.34 g (6.07 mmol) of the raw material C, and 15 ml of 1-propanol under a nitrogen stream. The mixture was stirred at 80° C. for 1.5 hours. After completion of the reaction, the reaction mixture was cooled to 20° C. to precipitate a solid, which was filtered off. The solid collected by filtration was washed with 1-propanol, and dried using a vacuum dryer to obtain 1.76 g of a compound (I-7) as a light yellow solid (yield: 84.9%).

The structure of the target product was identified by $^1$H-NMR.

The $^1$H-NMR spectrum data are shown below.

$^1$H-NMR (500 MHz, DMSO-d$_6$, TMS, δ ppm): 9.39 (s, 1H), 8.97 (s, 1H), 8.15 (s, 1H), 7.83 (d, 1H, J=7.5 Hz), 7.60 (d, 1H, J=7.5 Hz), 7.33 (dd, 1H, J=7.5 Hz, 7.5 Hz), 7.18 (d, 1H, J=3.0 Hz), 7.16 (dd, 1H, J=7.5 Hz, 7.5 Hz), 6.76 (d, 1H, J=8.5 Hz), 6.70 (dd, 1H, J=3.0 Hz, 8.5 Hz), 4.33 (t, 2H, J=7.5 Hz), 1.66 (tt, 2H, H=7.5 Hz, 7.5 Hz), 1.39 (tq, 2H, J=7.5 Hz, 7.0 Hz), 0.95 (t, 3H, J=7.0 Hz)

A four-necked reactor equipped with a thermometer was charged with 2.00 g (12.1 mmol) of 2-hydrazinobenzothiazole and 20 ml of DMF under a nitrogen stream to prepare a homogeneous solution. After the addition of 8.36 g (60.5 mmol) of potassium carbonate and 3.08 g (14.5 mmol) of 1-iodohexane to the solution, the mixture was stirred at 50° C. for 7 hours. After completion of the reaction, the reaction mixture was cooled to 20° C., added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio)) to obtain 2.10 g of a raw material D as a white solid (yield: 69.6%).

The structure of the target product was identified by $^1$H-NMR.

The $^1$H-NMR spectrum data are shown below.

$^1$H-NMR (500 MHz, CDCl$_3$, TMS, δ ppm): 7.60 (dd, 1H, J=1.0 Hz, 8.0 Hz), 7.53 (dd, 1H, J=1.0 Hz, 8.0 Hz), 7.27 (ddd, 1H, J=1.0 Hz, 8.0 Hz, 8.0 Hz), 7.06 (ddd, 1H, J=1.0 Hz, 8.0 Hz, 8.0 Hz), 4.22 (s, 2H), 3.74 (t, 2H, J=7.5 Hz), 1.69-1.76 (m, 2H), 1.29-1.42 (m, 6H), 0.89 (t, 3H, J=7.0 Hz)

Step 2: Synthesis of Compound (I-8)

A four-necked reactor equipped with a thermometer was charged with 504 mg (3.65 mmol) of 2,5-dihydroxybenzaldehyde, 1.00 g (4.01 mmol) of the raw material D, and 10 ml of 1-propanol under a nitrogen stream. The mixture was stirred at 80° C. for 3 hours. After completion of the reaction, the reaction mixture was cooled to 20° C. to precipitate a solid, which was filtered off. The solid collected by filtration was washed with 1-propanol, and dried using a vacuum dryer to obtain 1.20 g of a compound (I-8) as a light yellow solid (yield: 88.8%).

The structure of the target product was identified by $^1$H-NMR.

The $^1$H-NMR spectrum data are shown below.

$^1$H-NMR (500 MHz, DMSO-d$_6$, TMS, δ ppm): 9.39 (s, 1H), 8.97 (s, 1H), 8.15 (s, 1H), 7.83 (dd, 1H, J=1.0 Hz, 8.0 Hz), 7.60 (dd, 1H, J=1.0 Hz, 8.0 Hz), 7.33 (ddd, 1H, J=1.0

Hz, 7.5 Hz, 8.0 Hz), 7.18 (d, 1H, J=3.0 Hz), 7.16 (ddd, 1H, J=1.0 Hz, 7.5 Hz, 8.0 Hz), 6.76 (d, 1H, J=8.5 Hz), 6.70 (dd, 1H, J=3.0 Hz, 8.5 Hz), 4.32 (t, 2H, J=7.0 Hz), 1.64-1.70 (m, 2H), 1.25-1.39 (m, 6H), 0.86 (t, 3H, J=7.5 Hz)

Example 9

Synthesis of Compound (I-9)

Compound (I-9)

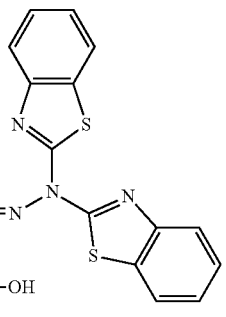

Step 1: Synthesis of Raw Material E

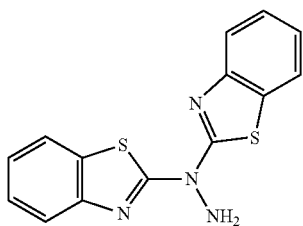

Raw material E

A four-necked reactor equipped with a thermometer was charged with 1.00 g (6.05 mmol) of 2-hydrazinobenzothiazole and 15 ml of THF under a nitrogen stream to prepare a homogeneous solution. 4.5 ml (7.26 mmol) of lithium hexamethyldisilazane (26% THF solution) was slowly added dropwise to the solution at 0° C., and the mixture was stirred at 0° C. for 30 minutes. After the addition of 1.23 g (7.26 mmol) of 2-chlorobenzothiazole to the solution, the mixture was stirred at 25° C. for 3 hours. After completion of the reaction, the reaction mixture was added to 100 ml of water, and extracted with 100 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio)) to obtain 511 mg of a raw material E as a light yellow solid (yield: 28.3%).

The structure of the target product was identified by $^1$H-NMR.

The $^1$H-NMR spectrum data are shown below.

$^1$H-NMR (400 MHz, DMSO-d$_6$, TMS, δ ppm): 7.97 (d, 2H, J=7.5 Hz), 7.74 (d, 2H, J=8.0 Hz), 7.42 (dd, 2H, J=7.8 Hz, 8.0 Hz), 7.27 (dd, 2H, J=7.5 Hz, 7.8 Hz), 6.55 (s, 2H)

Step 2: Synthesis of Compound (I-9)

A four-necked reactor equipped with a thermometer was charged with 197 mg (1.43 mmol) of 2,5-dihydroxybenzaldehyde, 511 mg (1.71 mmol) of the raw material E, 32.5 mg (0.14 mmol) of (±)-10-camphorsulfonic acid, and 10 ml of 1-propanol under a nitrogen stream. The mixture was stirred at 80° C. for 2.5 hours. After completion of the reaction, the reaction mixture was cooled to 20° C. to precipitate a solid, which was filtered off. The solid collected by filtration was washed with 1-propanol, and dried using a vacuum dryer to obtain 401 mg of a compound (I-9) as a light yellow solid (yield: 66.9%).

The structure of the target product was identified by $^1$H-NMR.

The $^1$H-NMR spectrum data are shown below.

$^1$H-NMR (500 MHz, THF-d$_8$, TMS, δ ppm): 8.39 (s, 1H), 7.40 (s, 1H), 6.31 (s, 1H), 6.19 (dd, 2H, J=1.0 Hz, 8.0 Hz), 6.12 (dd, 2H, J=1.0 Hz, 8.0 Hz), 5.71 (ddd, 2H, J=1.0 Hz, 7.5 Hz, 8.0 Hz), 5.59 (ddd, 2H, J=1.0 Hz, 7.5 Hz, 8.0 Hz), 5.47 (d, 1H, J=3.0 Hz), 5.12 (dd, 1H, J=3.0 Hz, 9.0 Hz), 5.08 (d, 1H, J=9.0 Hz)

Example 10

Synthesis of Compound (I-10)

Compound (I-10)

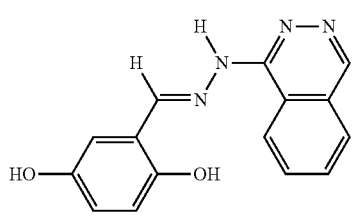

A four-necked reactor equipped with a thermometer was charged with 197 mg (1.43 mmol) of 2,5-dihydroxybenzaldehyde, 281 mg (1.43 mmol) of 1-hydrazinophthalazine hydrochloride, 32.5 mg (0.14 mmol) of (±)-10-camphorsulfonic acid, and 10 ml of ethanol under a nitrogen stream. The mixture was stirred at 25° C. for 2 hours. After completion of the reaction, a solid precipitate was filtered off. The solid collected by filtration was washed with ethanol, and dried using a vacuum dryer to obtain 305 mg of a compound (I-10) as a yellow solid (yield: 76.1%).

The structure of the target product was identified by $^1$H-NMR.

The $^1$H-NMR spectrum data are shown below.

$^1$H-NMR (500 MHz, DMSO-d$_6$, TMS, δ ppm): 14.486 (br, 1H), 14.150 (br, 1H), 9.77 (s, 1H), 9.30 (s, 1H), 9.20 (d, 1H, J=8.0 Hz), 9.06 (s, 1H), 8.27-8.14 (m, 3H), 7.76 (d, 1H, J=2.5 Hz), 6.89 (dd, 1H, J=3.0 Hz, 8.5 Hz), 6.84 (d, 1H, J=8.5 Hz)

Example 11

Synthesis of Compound (I-11)

Compound (I-11)

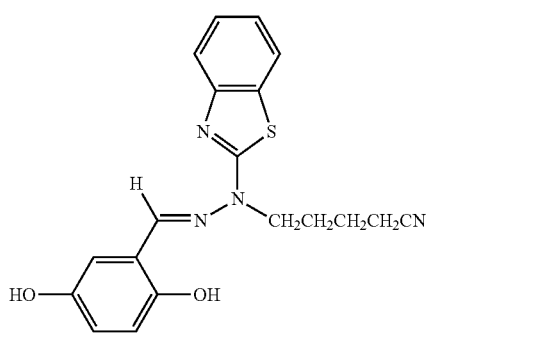

Step 1: Synthesis of Raw Material F

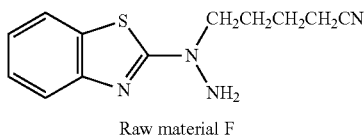

Raw material F

A four-necked reactor equipped with a thermometer was charged with 5.00 g (30.3 mmol) of 2-hydrazinobenzothiazole and 100 ml of DMF under a nitrogen stream to prepare a homogeneous solution. After the addition of 20.9 g (152 mmol) of potassium carbonate and 5.17 g (30.3 mmol) of 5-bromovaleronitrile to the solution, the mixture was stirred at 60° C. for 8 hours. After completion of the reaction, the reaction mixture was cooled to 20° C., added to 500 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=60:40 (volume ratio)) to obtain 3.41 g of a raw material F as a white solid (yield: 45.7%).

The structure of the target product was identified by $^1$H-NMR.

The $^1$H-NMR spectrum data are shown below.

$^1$H-NMR (400 MHz, CDCl$_3$, TMS, δ ppm): 7.60 (d, 1H, J=7.8 Hz), 7.51 (d, 1H, J=8.1 Hz), 7.28 (dd, 1H, J=7.3 Hz, 8.1 Hz), 7.07 (dd, 1H, J=7.3 Hz, 7.8 Hz), 4.23 (s, 2H), 3.81 (t, 2H, J=6.9 Hz), 2.46 (t, 2H, J=7.1 Hz), 1.88-1.95 (m, 2H), 1.71-1.79 (m, 2H)

Step 2: Synthesis of Compound (I-11)

A four-necked reactor equipped with a thermometer was charged with 1.62 g (11.7 mmol) of 2,5-dihydroxybenzaldehyde, 2.89 g (11.7 mmol) of the raw material F synthesized in the step 1, and 30 ml of 1-propanol under a nitrogen stream. The mixture was stirred at 80° C. for 7 hours. After completion of the reaction, the reaction mixture was cooled to 20° C. to precipitate a solid, which was filtered off. The solid collected by filtration was washed with 1-propanol, and dried using a vacuum dryer to obtain 2.92 g of a compound (I-11) as a white solid (yield: 68.2%).

The structure of the target product was identified by $^1$H-NMR.

The $^1$H-NMR spectrum data are shown below.

$^1$H-NMR (400 MHz, DMSO-d$_6$, TMS, δ ppm): 9.36 (s, 1H), 8.94 (s, 1H), 8.13 (s, 1H), 7.81 (d, 1H, J=7.3 Hz), 7.57 (d, 1H, J=7.6 Hz), 7.30 (dd, 1H, J=7.6 Hz, 8.0 Hz), 7.14 (d, 1H, J=3.2 Hz), 7.13 (dd, 1H, J=7.3 Hz, 8.0 Hz), 6.73 (d, 1H, J=8.7 Hz), 6.67 (dd, 1H, J=3.2 Hz, 8.7 Hz), 4.34 (t, 2H, J=7.1 Hz), 2.57 (t, 2H, J=7.2 Hz), 1.72-1.79 (m, 2H), 1.59-1.66 (m, 2H)

Example 12

Synthesis of Compound (I-12)

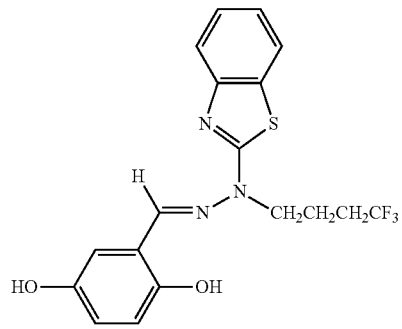

Compound (I-12)

Step 1: Synthesis of Raw Material G

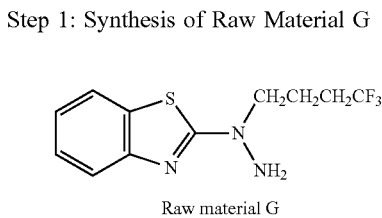

Raw material G

A four-necked reactor equipped with a thermometer was charged with 1.45 g (8.75 mmol) of 2-hydrazinobenzothiazole and 20 ml of DMF under a nitrogen stream to prepare a homogeneous solution. After the addition of 3.63 g (26.3 mmol) of potassium carbonate and 2.50 g (10.5 mmol) of 1,1,1-trifluoro-4-iodobutane the solution, the mixture was stirred at 80° C. for 8 hours. After completion of the reaction, the reaction mixture was cooled to 20° C., added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=85:15 (volume ratio)) to obtain 961 mg of a raw material G as a white solid (yield: 39.9%).

The structure of the target product was identified by $^1$H-NMR.

The $^1$H-NMR spectrum data are shown below.

$^1$H-NMR (500 MHz, CDCl$_3$, TMS, δ ppm): 7.61 (d, 1H, J=8.0 Hz), 7.54 (d, 1H, J=7.8 Hz), 7.30 (dd, 1H, J=7.8 Hz, 7.8 Hz), 7.09 (dd, 1H, J=7.8 Hz, 8.0 Hz), 4.24 (s, 2H), 3.81 (t, 2H, J=7.0 Hz), 2.16-2.26 (m, 2H), 1.99-2.05 (m, 2H)

Step 2: Synthesis of Compound (I-12)

A four-necked reactor equipped with a thermometer was charged with 372 mg (2.69 mmol) of 2,5-dihydroxybenzaldehyde, 740 mg (2.69 mmol) of the raw material G synthesized in the step 1, and 10 ml of 1-propanol under a nitrogen stream. The mixture was stirred at 80° C. for 6 hours. After completion of the reaction, the reaction mixture was cooled to 20° C. to precipitate a solid, which was filtered off. The solid collected by filtration was washed with 1-propanol, and dried using a vacuum dryer to obtain 916 mg of a compound (I-12) as a white solid (yield: 86.1%).

The structure of the target product was identified by $^1$H-NMR.

The $^1$H-NMR spectrum data are shown below.

$^1$H-NMR (500 MHz, DMSO-d$_6$, TMS, δ ppm): 9.39 (s, 1H), 8.98 (s, 1H), 8.18 (s, 1H), 7.85 (d, 1H, J=7.8 Hz), 7.61 (d, 1H, J=8.1 Hz), 7.35 (dd, 1H, J=7.3 Hz, 8.1 Hz), 7.16-7.19 (m, 2H), 6.76 (d, 1H, J=9.0 Hz), 6.71 (dd, 1H, J=3.0 Hz, 9.0 Hz), 4.42 (t, 2H, J=7.5 Hz), 2.40-2.50 (m, 2H), 1.88-1.97 (m, 2H)

Example 13

Synthesis of Compound (I-13)

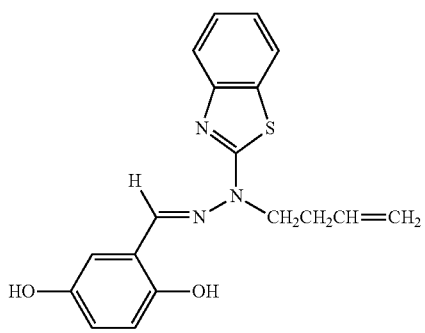

Compound (I-13)

Step 1: Synthesis of Raw Material H

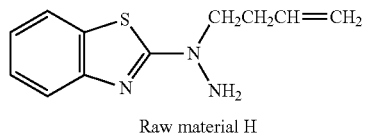

Raw material H

A four-necked reactor equipped with a thermometer was charged with 3.00 g (18.2 mmol) of 2-hydrazinobenzothiazole and 30 ml of DMF under a nitrogen stream to prepare a homogeneous solution. After the addition of 7.55 g (54.6 mmol) of potassium carbonate and 2.94 g (21.8 mmol) of 4-bromo-1-butene to the solution, the mixture was stirred at 80° C. for 4 hours. After completion of the reaction, the reaction mixture was cooled to 20° C., added to 300 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=85:15 (volume ratio)) to obtain 1.44 g of a raw material H as a white solid (yield: 36.1%).

The structure of the target product was identified by $^1$H-NMR.

The $^1$H-NMR spectrum data are shown below.

$^1$H-NMR (500 MHz, CDCl$_3$, TMS, δ ppm): 7.60 (d, 1H, J=7.8 Hz), 7.54 (d, 1H, J=7.5 Hz), 7.30 (dd, 1H, J=7.8 Hz, 7.8 Hz), 7.07 (dd, 1H, J=7.5 Hz, 7.8 Hz), 5.89 (ddt, 1H, J=10.3 Hz, 17.0 Hz, 7.0 Hz), 5.18 (dd, 1H, J=1.5 Hz, 17.0 Hz), 5.09 (dd, 1H, J=1.5, 10.3 Hz), 4.27 (s, 2H), 3.86 (t, 2H, J=7.0 Hz), 2.53 (dt, 2H, J=7.0 Hz, 7.0 Hz)

Step 2: Synthesis of Compound (I-13)

A four-necked reactor equipped with a thermometer was charged with 630 mg (4.56 mmol) of 2,5-dihydroxybenzaldehyde, 1.00 g (4.56 mmol) of the raw material H synthesized in the step 1, and 15 ml of 1-propanol under a nitrogen stream. The mixture was stirred at 80° C. for 6 hours. After completion of the reaction, the reaction mixture was cooled to 20° C. to precipitate a solid, which was filtered off. The solid collected by filtration was washed with 1-propanol, and dried using a vacuum dryer to obtain 760 mg of a compound (I-13) as a white solid (yield: 49.1%).

The structure of the target product was identified by $^1$H-NMR.

The $^1$H-NMR spectrum data are shown below.

$^1$H-NMR (500 MHz, CDCl$_3$, TMS, δ ppm): 9.77 (s, 1H), 7.80 (s, 1H), 7.693 (d, 1H, J=7.8 Hz), 7.687 (d, 1H, J=7.8 Hz), 7.37 (dd, 1H, J=7.5 Hz, 7.8 Hz), 7.19 (dd, 1H, J=7.5 Hz, 7.8 Hz), 6.94 (d, 1H, J=9.0 Hz), 6.83 (dd, 1H, J=3.0 Hz, 9.0 Hz), 6.78 (d, 1H, J=3.0 Hz), 5.90 (ddt, 1H, J=10.3 Hz, 17.0 Hz, 7.5 Hz), 5.19 (dd, 1H, J=1.5 Hz, 17.0 Hz), 5.13 (dd, 1H, J=1.5 Hz, 10.3 Hz), 4.71 (s, 1H), 4.45 (t, 2H, J=7.5 Hz), 2.56 (dt, 2H, J=7.5 Hz, 7.5 Hz)

Example 14

Synthesis of Compound (I-14)

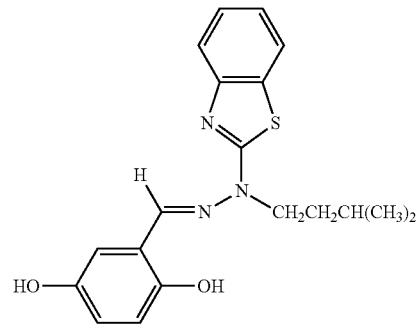

Compound (I-14)

Step 1: Synthesis of Raw Material I

A four-necked reactor equipped with a thermometer was charged with 3.00 g (18.2 mmol) of 2-hydrazinobenzothiazole and 20 ml of THF under a nitrogen stream to prepare a homogeneous solution. 11.4 ml (18.2 mmol) of lithium hexamethyldisilazane (26% THF solution) was slowly added dropwise to the solution at 0° C., and the mixture was stirred at 0° C. for 30 minutes. After the addition of 2.9 ml (21.8 mmol) of 1-iodo-3-methylbutane to the reaction mixture, the mixture was stirred at room temperature for 6 hours. After completion of the reaction, the reaction mixture was added to 100 ml of water, and extracted with 150 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio)) to obtain 2.07 g of a raw material I as a white solid (yield: 48.2%).

The structure of the target product was identified by $^1$H-NMR.

The $^1$H-NMR spectrum data are shown below.

$^1$H-NMR (500 MHz, CDCl$_3$, TMS, δ ppm): 7.59 (d, 1H, J=8.5 Hz), 7.53 (d, 1H, J=8.0 Hz), 7.27 (dd, 1H, J=7.8 Hz, 8.0 Hz), 7.06 (dd, 1H, J=7.8 Hz, 8.5 Hz), 4.21 (s, 2H), 3.75

(t, 2H, J=7.5 Hz), 1.63-1.70 (m, 1H), 1.60 (dt, 2H, J=7.0 Hz, 7.5 Hz), 0.97 (d, 6H, J=6.5 Hz)

Step 2: Synthesis of Compound (I-14)

A four-necked reactor equipped with a thermometer was charged with 1.21 g (8.78 mmol) of 2,5-dihydroxybenzaldehyde, 2.07 g (8.78 mmol) of the raw material I synthesized in the step 1, and 15 ml of 2-propanol under a nitrogen stream. The mixture was stirred at 80° C. for 1.5 hours. After completion of the reaction, the reaction mixture was cooled to 20° C. to precipitate a solid, which was filtered off. The solid collected by filtration was washed with 2-propanol, and dried using a vacuum dryer to obtain 1.36 g of a compound (I-14) as a white solid (yield: 43.6%).

The structure of the target product was identified by $^1$H-NMR.

The $^1$H-NMR spectrum data are shown below.

$^1$H-NMR (500 MHz, DMSO-$d_6$, TMS, δ ppm): 9.38 (s, 1H), 8.97 (s, 1H), 8.12 (s, 1H), 7.83 (d, 1H, J=8.0 Hz), 7.59 (d, 1H, J=8.0 Hz), 7.33 (dd, 1H, J=7.5 Hz, 8.0 Hz), 7.18 (d, 1H, J=3.0 Hz), 7.16 (dd, 1H, J=7.5 Hz, 8.0 Hz), 6.75 (d, 1H, J=9.0 Hz), 6.70 (dd, 1H, J=3.0 Hz, 9.0 Hz), 4.34 (t, 2H, J=7.5 Hz), 1.63-1.74 (m, 1H), 1.55 (dt, 2H, J=7.0 Hz, 7.5 Hz), 0.99 (d, 6H, J=6.5 Hz)

Example 15

Synthesis of Compound (I-15)

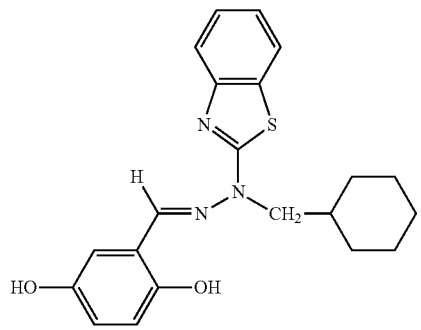

Compound (I-15)

Step 1: Synthesis of Raw Material J

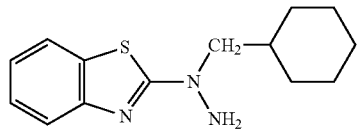

Raw material J

A four-necked reactor equipped with a thermometer was charged with 3.00 g (18.2 mmol) of 2-hydrazinobenzothiazole and 30 ml of DMF under a nitrogen stream to prepare a homogeneous solution. After the addition of 7.55 g (54.6 mmol) of potassium carbonate and 3.86 g (21.8 mmol) of (bromomethyl)cyclohexane to the solution, the mixture was stirred at 80° C. for 9 hours. After completion of the reaction, the reaction mixture was cooled to 20° C., added to 300 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=85:15 (volume ratio)) to obtain 2.36 g of a raw material J as a white solid (yield: 49.7%).

The structure of the target product was identified by $^1$H-NMR.

The $^1$H-NMR spectrum data are shown below.

$^1$H-NMR (400 MHz, CDCl$_3$, TMS, δ ppm): 7.58 (d, 1H, J=8.0 Hz), 7.51 (d, 1H, J=8.1 Hz), 7.26 (dd, 1H, J=7.0 Hz, 8.1 Hz), 7.04 (dd, 1H, J=7.0 Hz, 8.0 Hz), 4.24 (s, 2H), 3.59 (d, 2H, J=7.4 Hz), 1.84-1.92 (m, 1H), 1.67-1.77 (m, 5H), 1.16-1.29 (m, 3H), 1.02-1.13 (m, 2H)

Step 2: Synthesis of Compound (I-15)

A four-necked reactor equipped with a thermometer was charged with 1.06 g (7.65 mmol) of 2,5-dihydroxybenzaldehyde, 2.00 g (7.65 mmol) of the raw material J synthesized in the step 1, and 20 ml of 1-propanol under a nitrogen stream. The mixture was stirred at 80° C. for 5 hours. After completion of the reaction, the reaction mixture was cooled to 20° C. to precipitate a solid, which was filtered off. The solid collected by filtration was washed with 1-propanol, and dried using a vacuum dryer to obtain 2.00 g of a compound (I-15) as a white solid (yield: 70.8%).

The structure of the target product was identified by $^1$H-NMR.

The $^1$H-NMR spectrum data are shown below.

$^1$H-NMR (400 MHz, DMSO-$d_6$, TMS, δ ppm): 9.33 (s, 1H), 8.93 (s, 1H), 8.11 (s, 1H), 7.79 (d, 1H, J=7.5 Hz), 7.55 (d, 1H, J=7.8 Hz), 7.28 (dd, 1H, J=7.8 Hz, 7.8 Hz), 7.15 (s, 1H), 7.11 (dd, 1H, J=7.5 Hz, 7.8 Hz), 6.72 (d, 1H, J=8.7 Hz), 6.66 (d, 1H, J=8.7 Hz), 4.17 (d, 2H, J=7.3 Hz), 1.82-1.92 (m, 1H), 1.56-1.63 (m, 5H), 1.01-1.19 (m, 5H)

Example 16

Synthesis of Compound (I-16)

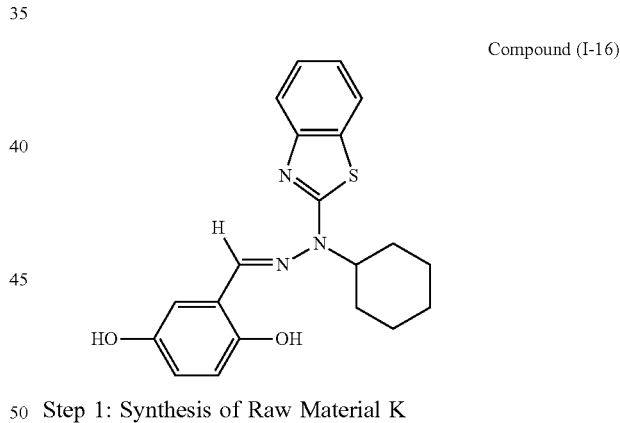

Compound (I-16)

Step 1: Synthesis of Raw Material K

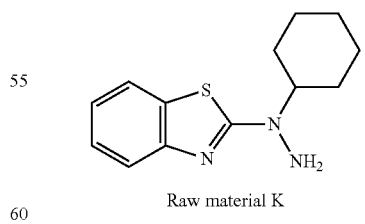

Raw material K

A four-necked reactor equipped with a thermometer was charged with 2.50 g (16.6 mmol) of cyclohexylhydrazine hydrochloride and 8 ml of triethylamine under a nitrogen stream to prepare a homogeneous solution. After the addition of 5.63 g (33.2 mmol) of 2-chlorobenzothiazole to the solution, the mixture was stirred at 80° C. for 5 hours. After completion of the reaction, the reaction mixture was cooled to 20° C., added to 150 ml of a saturated sodium hydrogen carbonate aqueous solution, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio)) to obtain 1.02 g of a raw material K as a white solid (yield: 22.3%).

The structure of the target product was identified by $^1$H-NMR.

The $^1$H-NMR spectrum data are shown below.

$^1$H-NMR (400 MHz, CDCl$_3$, TMS, δ ppm): 7.58 (d, 1H, J=7.8 Hz), 7.52 (d, 1H, J=8.2 Hz), 7.26 (dd, 1H, J=7.4 Hz, 8.2 Hz), 7.05 (dd, 1H, J=7.4 Hz, 7.8 Hz), 4.25-4.32 (m, 1H), 4.04 (s, 2H), 1.84-1.88 (m, 4H), 1.68-1.73 (m, 1H), 1.43-1.59 (m, 4H), 1.08-1.19 (m, 1H)

Step 2: Synthesis of Compound (I-16)

A four-necked reactor equipped with a thermometer was charged with 510 mg (3.69 mmol) of 2,5-dihydroxybenzaldehyde, 1.02 g (3.69 mmol) of the raw material K synthesized in the step 1, and 10 ml of 2-propanol under a nitrogen stream. The mixture was stirred at 80° C. for 3 hours. After completion of the reaction, the reaction mixture was cooled to 20° C. to precipitate a solid, which was filtered off. The solid collected by filtration was washed with 2-propanol, and dried using a vacuum dryer to obtain 685 mg of a compound (I-16) as a white solid (yield: 46.9%).

The structure of the target product was identified by $^1$H-NMR.

The $^1$H-NMR spectrum data are shown below.

$^1$H-NMR (400 MHz, DMSO-d$_6$, TMS, δ ppm): 9.38 (s, 1H), 8.93 (s, 1H), 8.37 (s, 1H), 7.77 (d, 1H, J=7.3 Hz), 7.56 (d, 1H, J=7.8 Hz), 7.28 (dd, 1H, J=7.8 Hz, 7.8 Hz), 7.15 (d, 1H, J=2.8 Hz), 7.11 (dd, 1H, J=7.3 Hz, 7.8 Hz), 6.72 (d, 1H, J=8.7 Hz), 6.67 (dd, 1H, J=2.8 Hz, 8.7 Hz), 4.58 (tt, 1H, J=3.7 Hz, 11.9 Hz), 2.36-2.45 (m, 2H), 1.76-1.86 (m, 4H), 1.65-1.68 (m, 1H), 1.38-1.48 (m, 2H), 1.16-1.25 (m, 1H)

The reaction solvent, the use or non-use of column purification, and the yield of the reaction for producing the compound (I-1) (Examples 1a, 1b, and 1c), the reaction for producing the compound (I-2) (Examples 2a and 2b), and the reaction for producing the compound (I-5) (Examples 5a and 5b) are shown in Table 1.

TABLE 1

| | Product | Reaction solvent | Column purification | Yield (%) |
|---|---|---|---|---|
| Example 1a | Compound (I-1) | Methanol | Not Performed | 91.7 |
| Example 1b | Compound (I-1) | 1-Propanol | Not performed | 92.5 |
| Example 1c | Compound (I-1) | Tetrahydrofuran | Performed | 75.9 |
| Example 2a | Compound (I-2) | Ethanol | Not performed | 95.9 |
| Example 2b | Compound (I-2) | Tetrahydrofuran | Performed | 82.5 |
| Example 5a | Compound (I-5) | Ethanol | Not performed | 90.7 |
| Example 5b | Compound (I-5) | Tetrahydrofuran | Performed | 70.5 |

As shown in Table 1, the target product was obtained in high yield in Examples 1, 2, and 5 using the alcohol-based solvent or the ether-based solvent.

The target product having high purity could be obtained in high yield when using the alcohol-based solvent (Examples 1a, 1b, 2a, and 5a) as compared with the case of using the ether-based solvent (THF) (Examples 1c, 2b, and 5b).

Note that precipitation of crystals was not observed after completion of the reaction when using the ether-based solvent (THF). The solid obtained after evaporating the solvent under reduced pressure was significantly colored, and it was necessary to perform column purification.

Reference Example 1

Synthesis of Compound 1r

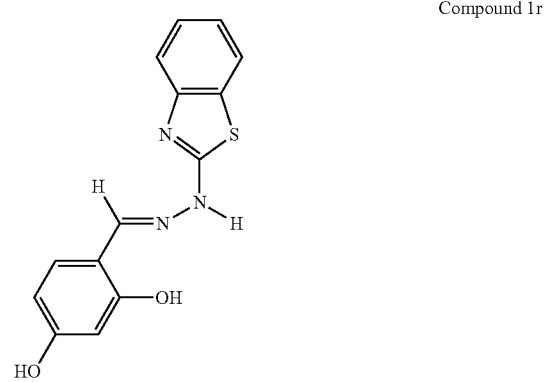 [SMILES: Oc1ccc(/C=N/Nc2nc3ccccc3s2)c(O)c1]

Compound 1r

A four-necked reactor equipped with a thermometer was charged with 10.0 g (72.4 mol) of 2,4-dihydroxybenzaldehyde and 150 ml of ethanol under a nitrogen stream to prepare a homogeneous solution. After the addition of 13.0 g (79.6 mol) of 2-hydrazinobenzothiazole to the solution, the mixture was stirred at 25° C. for 2 hours. After completion of the reaction, a solid precipitate was filtered off. The solid collected by filtration was washed with ethanol, and dried using a vacuum dryer to obtain 13.0 g of a compound 1r as a light yellow solid (yield: 63.9%).

The structure of the target product was identified by $^1$H-NMR.

The $^1$H-NMR spectrum data are shown below.

$^1$H-NMR (500 MHz, DMSO-d$_6$, TMS, δ ppm): 12.00 (brs, 1H), 9.39 (s, 1H), 9.24 (s, 1H), 7.96 (s, 1H), 7.76 (s, 1H), 7.41 (d, 1H, J=7.5 Hz), 7.28 (dd, 1H, J=7.5 Hz, 7.5 Hz), 7.20 (d, 1H, J=2.0 Hz), 7.09 (dd, 1H, J=7.5 Hz, 7.5 Hz), 6.92 (dd, 1H, J=2.0 Hz, 8.0 Hz), 6.79 (d, 1H, J=8.0 Hz)

Reference Example 2

Synthesis of Compound 2r

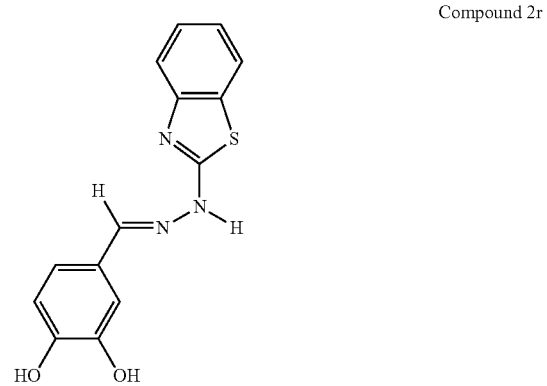 [SMILES: Oc1ccc(/C=N/Nc2nc3ccccc3s2)cc1O]

Compound 2r

A four-necked reactor equipped with a thermometer was charged with 10.0 g (72.4 mol) of 3,4-dihydroxybenzaldehyde and 150 ml of ethanol under a nitrogen stream to prepare a homogeneous solution. After the addition of 13.0 g (79.6 mol) of 2-hydrazinobenzothiazole to the solution, the mixture was stirred at 25° C. for 5 hours. After completion of the reaction, a solid precipitate was filtered off. The solid collected by filtration was washed with ethanol, and dried using a vacuum dryer to obtain 17.0 g of a compound 2r as a light yellow solid (yield: 81.2%).

The structure of the target product was identified by $^1$H-NMR.

The $^1$H-NMR spectrum data are shown below.

$^1$H-NMR (500 MHz, DMSO-$d_6$, TMS, δ ppm): 11.95 (brs, 1H), 10.58 (brs, 1H), 9.90 (s, 1H), 8.34 (s, 1H), 7.71 (d, 1H, J=8.0 Hz), 7.39 (d, 1H, J=8.0 Hz), 7.26-7.33 (m, 2H), 7.07 (dd, 1H, J=8.0 Hz, 8.0 Hz), 6.37 (dd, 1H, J=2.5 Hz, 8.3 Hz), 6.35 (d, 1H, J=2.5 Hz)

Production Example 1

Synthesis of Polymerizable Compound 1

A four-necked reactor equipped with a thermometer was charged with 5.0 g (17.5 mmol) of the compound (I-1) synthesized in Example 1a, 12.8 g (43.8 mmol) of 4-(6-acryloylhex-1-yloxy)benzoic acid (manufactured by DKSH Japan K.K.), 0.64 g (5.2 mmol) of 4-(dimethylamino)pyridine, and 200 ml of N-methylpyrrolidone under a nitrogen stream to prepare a homogeneous solution. After the addition of 10.1 g (52.6 mmol) of 1-ethyl-3-(3-dimethylaminopropyl)carbodiimide hydrochloride (WSC) to the solution, the mixture was stirred at 25° C. for 12 hours. After completion of the reaction, the reaction mixture was added to 1 l of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=8:2 (volume ratio)) to obtain 8.48 g of a polymerizable compound 1 as a light yellow solid (yield: 58.1%).

The structure of the target product was identified by $^1$H-NMR and mass spectroscopy.

The $^1$H-NMR spectrum data and the mass spectrum data are shown below.

$^1$H-NMR (500 MHz, DMSO-$d_6$, TMS, δ ppm): 12.30 (br, 1H), 8.19 (s, 1H), 8.17-8.12 (m, 4H), 7.76 (d, 1H, J=3.0 Hz), 7.68 (d, 1H, J=7.5 Hz), 7.45-7.39 (m, 3H), 7.28 (t, 1H, J=8.0 Hz), 7.18-7.14 (m, 4H), 7.09 (t, 1H, J=8.0 Hz), 6.33 (dd, 2H, J=1.5 Hz, 17.5 Hz), 6.18 (dd, 2H, J=10.5 Hz, 17.5 Hz), 5.944 (dd, 1H, J=1.5 Hz, 10.5 Hz), 5.941 (dd, 1H, J=1.5 Hz, 10.5 Hz), 4.14-4.10 (m, 8H), 1.80-1.75 (m, 4H), 1.69-1.63 (m, 4H), 1.53-1.38 (m, 8H)

LCMS (APCI) calcd for $C_{46}H_{47}N_3O_{10}S$: 833 [M$^+$]. Found: 833.

Production Example 2

Synthesis of Polymerizable Compound 2

Polymerizable compound 1

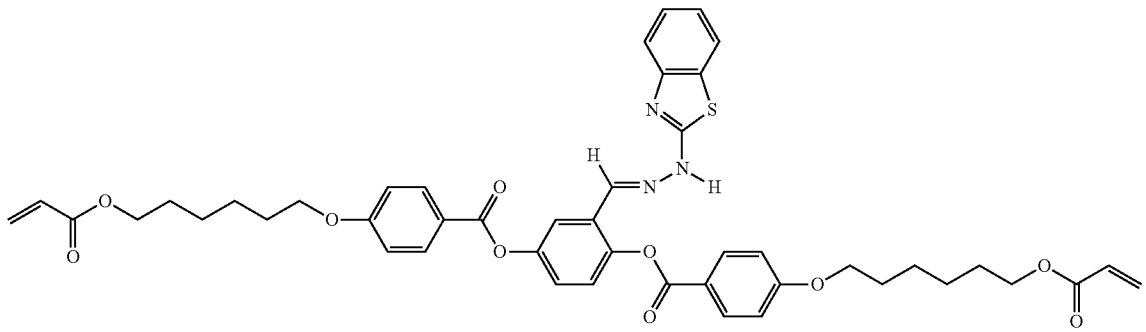

Polymerizable compound 2

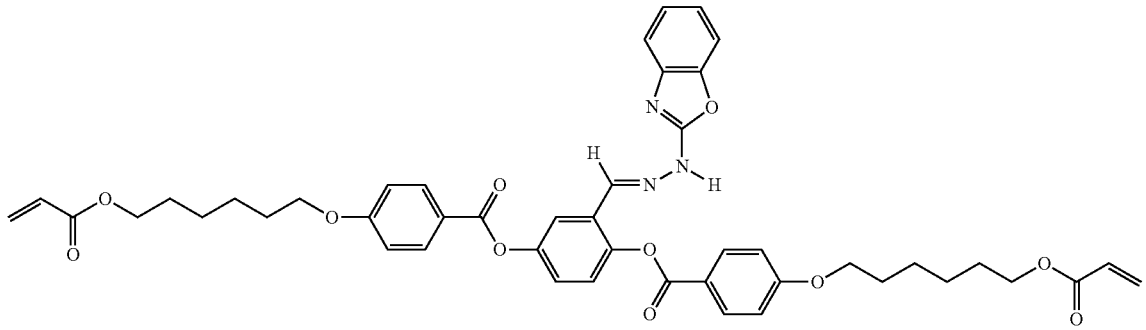

A four-necked reactor equipped with a thermometer was charged with 3.0 g (11.14 mmol) of the compound (I-2) synthesized in Example 2a, 8.14 g (27.85 mmol) of 4-(6-acryloylhex-1-yloxy)benzoic acid (manufactured by DKSH Japan K.K.), 0.68 g (5.57 mmol) of 4-(dimethylamino) pyridine, and 150 ml of N-methylpyrrolidone under a nitrogen stream to prepare a homogeneous solution. After the addition of 6.40 g (33.42 mmol) of WSC to the solution, the mixture was stirred at 25° C. for 12 hours. After completion of the reaction, the reaction mixture was added to 800 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=8:2 (volume ratio)) to obtain 5.06 g of a polymerizable compound 2 as a white solid (yield: 55.5%).

The structure of the target product was identified by $^1$H-NMR and mass spectroscopy.

The $^1$H-NMR spectrum data and the mass spectrum data are shown below.

$^1$H-NMR (500 MHz, DMSO-$d_6$, TMS, δ ppm): 12.20 (br, 1H), 8.28 (s, 1H), 8.17-8.12 (m, 4H), 7.82 (br, 1H), 7.46-7.40 (m, 3H), 7.32 (br, 1H), 7.20-7.14 (m, 5H), 7.08 (t, 1H, J=8.0 Hz), 6.33 (dd, 2H, J=1.5 Hz, 17.5 Hz), 6.18 (dd, 2H, J=10.5 Hz, 17.5 Hz), 5.94 (d, 2H, J=10.5 Hz), 4.14-4.10 (m, 8H), 1.80-1.75 (m, 4H), 1.69-1.63 (m, 4H), 1.51-1.38 (m, 8H)

LCMS (APCI) calcd for $C_{46}H_{47}N_3O_{11}$: 817 [M$^+$]. Found: 817.

Production Example 3

Synthesis of Polymerizable Compound 3

A four-necked reactor equipped with a thermometer was charged with 3.0 g (10.78 mmol) of the compound (I-3) synthesized in Example 3, 7.88 g (26.95 mmol) of 4-(6-acryloylhex-1-yloxy)benzoic acid (manufactured by DKSH Japan K.K.), 0.66 g (5.39 mmol) of 4-(dimethylamino) pyridine, and 150 ml of N-methylpyrrolidone under a nitrogen stream to prepare a homogeneous solution. After the addition of 6.20 g (32.34 mmol) of WSC to the solution, the mixture was stirred at 25° C. for 12 hours. After completion of the reaction, the reaction mixture was added to 800 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=8:2 (volume ratio)) to obtain 4.23 g of a polymerizable compound 3 as an orange solid (yield: 47.5%).

The structure of the target product was identified by $^1$H-NMR and mass spectroscopy.

The $^1$H-NMR spectrum data and the mass spectrum data are shown below.

$^1$H-NMR (400 MHz, CDCl$_3$, TMS, δ ppm): 8.35 (s, 1H), 8.20 (d, 2H, J=7.0 Hz), 8.18 (d, 2H, J=7.0 Hz), 7.95-7.96 (m, 2H), 7.79 (t, 2H, J=7.3 Hz), 7.32-7.53 (m, 5H), 7.17-7.24 (m, 2H), 7.00 (d, 2H, J=7.0 Hz), 7.98 (d, 2H, J=7.0 Hz), 6.41 (dd, 2H, J=0.9 Hz, 17.4 Hz), 6.13 (dd, 2H, J=10.5 Hz, 17.4 Hz), 5.82 (dd, 2H, J=0.9 Hz, 10.5 Hz), 4.19 (t, 4H, J=6.6 Hz), 4.05-4.08 (m, 4H), 1.79-1.89 (m, 4H), 1.65-1.77 (m, 4H), 1.46-1.59 (m, 8H)

LCMS (APCI) calcd for $C_{49}H_{50}N_2O_{10}$: 826 [M$^+$]. Found: 826.

Polymerizable compound 3

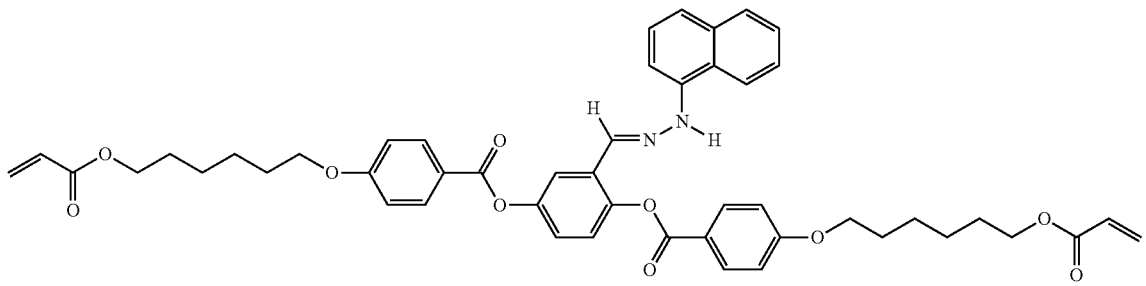

Production Example 4

Synthesis of Polymerizable Compound 4

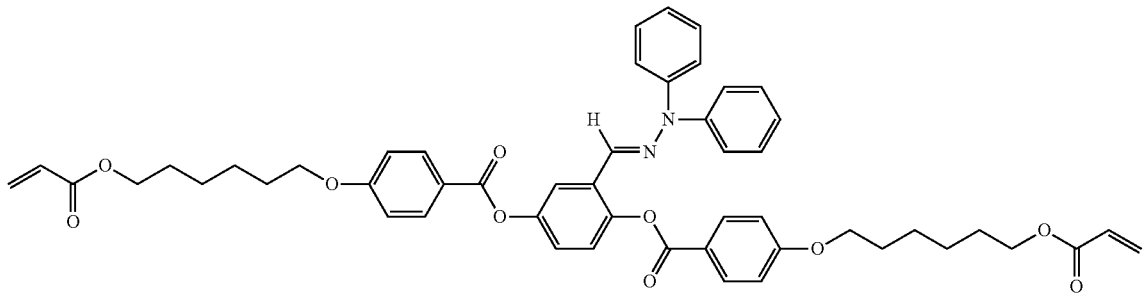

Polymerizable compound 4

A four-necked reactor equipped with a thermometer was charged with 3.0 g (9.86 mmol) of the compound (I-4) synthesized in Example 4, 7.20 g (24.64 mmol) of 4-(6-acryloylhex-1-yloxy)benzoic acid (manufactured by DKSH Japan K.K.), 0.60 g (4.93 mmol) of 4-(dimethylamino) pyridine, and 150 ml of N-methylpyrrolidone under a nitrogen stream to prepare a homogeneous solution. After the addition of 5.67 g (29.57 mmol) of WSC to the solution, the mixture was stirred at 25° C. for 12 hours. After completion of the reaction, the reaction mixture was added to 800 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=8:2 (volume ratio)) to obtain 4.37 g of a polymerizable compound 4 as a light yellow solid (yield: 52.0%).

The structure of the target product was identified by $^1$H-NMR.

The $^1$H-NMR spectrum data are shown below.

$^1$H-NMR (400 MHz, CDCl$_3$, TMS, δ ppm): 8.18 (d, 2H, J=8.7 Hz), 7.90 (d, 1H, J=2.7 Hz), 7.82 (d, 2H, J=8.7 Hz), 7.21-7.29 (m, 6H), 7.10-7.15 (m, 5H), 7.05 (t, 2H, J=7.3 Hz), 6.99 (d, 2H, J=9.2 Hz), 6.88 (d, 2H, J=9.2 Hz), 6.41 (dd, 2H, J=1.8 Hz, 17.4 Hz), 6.13 (dd, 2H, J=10.5 Hz, 17.4 Hz), 5.82 (dd, 2H, J=1.8 Hz, 10.5 Hz), 4.20 (t, 2H, J=6.4 Hz), 4.19 (t, 2H, J=6.4 Hz), 4.07 (t, 2H, J=6.4 Hz), 4.06 (t, 2H, J=6.4 Hz), 1.82-1.92 (m, 4H), 1.70-1.79 (m, 4H), 1.44-1.61 (m, 8H)

Production Example 5

Synthesis of Polymerizable Compound 5

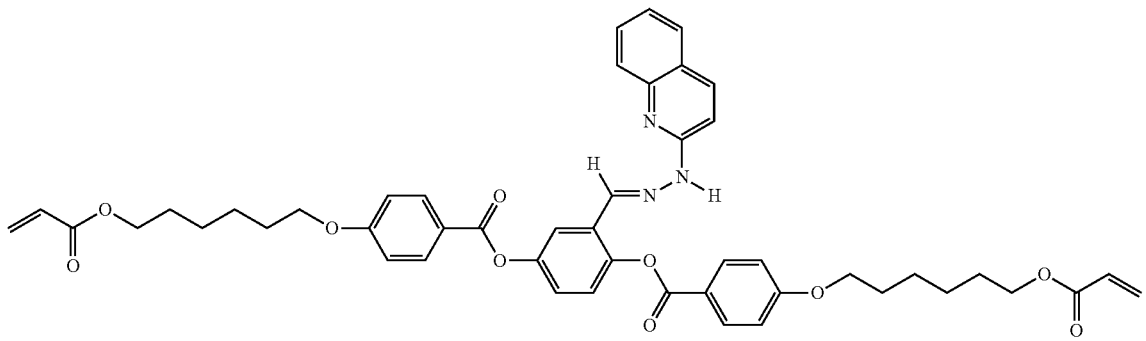

Polymerizable compound 5

A four-necked reactor equipped with a thermometer was charged with 3.0 g (10.74 mmol) of the compound (I-5) synthesized in Example 5a, 7.85 g (26.85 mmol) of 4-(6-acryloylhex-1-yloxy)benzoic acid (manufactured by DKSH Japan K.K.), 0.66 g (5.37 mmol) of 4-(dimethylamino) pyridine, and 150 ml of N-methylpyrrolidone under a nitrogen stream to prepare a homogeneous solution. After the addition of 6.18 g (32.22 mmol) of WSC to the solution, the mixture was stirred at 25° C. for 12 hours. After completion of the reaction, the reaction mixture was added to 800 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=8:2 (volume ratio)) to obtain 3.64 g of a polymerizable compound 5 as a yellow solid (yield: 40.9%).

The structure of the target product was identified by $^1$H-NMR.

The $^1$H-NMR spectrum data are shown below.

$^1$H-NMR (500 MHz, DMSO-d$_6$, TMS, δ ppm): 11.5 (s, 1H), 8.23 (s, 1H), 8.16 (d, 2H, J=9.0 Hz), 8.13 (d, 2H, J=9.0 Hz), 8.05 (d, 1H, J=9.0 Hz), 7.91 (d, 1H, J=2.5 Hz), 7.75 (d, 1H, J=8.0 Hz), 7.53-7.59 (m, 3H), 7.40 (d, 1H, J=9.0 Hz), 7.33 (ddd, 1H, J=2.0 Hz, 6.0 Hz, 8.0 Hz), 7.40 (d, 1H, J=9.0 Hz), 7.17 (d, 2H, J=9.0 Hz), 7.14 (d, 2H, J=9.0 Hz), 6.33 (dd, 2H, J=1.0 Hz, 17.3 Hz), 6.19 (dd, 2H, J=10.5 Hz, 17.3 Hz), 5.94 (dd, 2H, J=1.0 Hz, 10.5 Hz), 4.09-4.14 (m, 8H), 1.75-1.81 (m, 4H), 1.63-1.69 (m, 4H), 1.38-1.51 (m, 8H)

Production Example 6

Synthesis of Polymerizable Compound 6

A four-necked reactor equipped with a thermometer was charged with 0.55 g (1.84 mmol) of the compound (I-6) synthesized in Example 6, 1.34 g (4.59 mmol) of 4-(6-acryloylhex-1-yloxy)benzoic acid (manufactured by DKSH Japan K.K.), 0.11 g (0.92 mmol) of 4-(dimethylamino)pyridine, and 50 ml of N-methylpyrrolidone under a nitrogen stream to prepare a homogeneous solution. After the addition of 1.06 g (5.51 mmol) of WSC to the solution, the mixture was stirred at 25° C. for 15 hours. After completion of the reaction, the reaction mixture was added to 500 ml of water, and extracted with 200 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (n-hexane:ethyl acetate=7:3 (volume ratio)) to obtain 1.13 g of a polymerizable compound 6 as a light yellow solid (yield: 72.4%).

The structure of the target product was identified by $^1$H-NMR.

The $^1$H-NMR spectrum data are shown below.

$^1$H-NMR (500 MHz, CDCl$_3$, TMS, δ ppm): 8.201 (d, 2H, J=9.0 Hz), 8.196 (d, 2H, J=9.0 Hz), 7.91 (s, 1H), 7.73 (s, 1H), 7.61-7.64 (m, 2H), 7.32 (ddd, 1H, J=1.0 Hz, 7.5 Hz, 7.5 Hz), 7.23-7.28 (m, 1H), 7.11-7.18 (m, 2H), 7.02 (d, 2H, Polymerizable compound 6

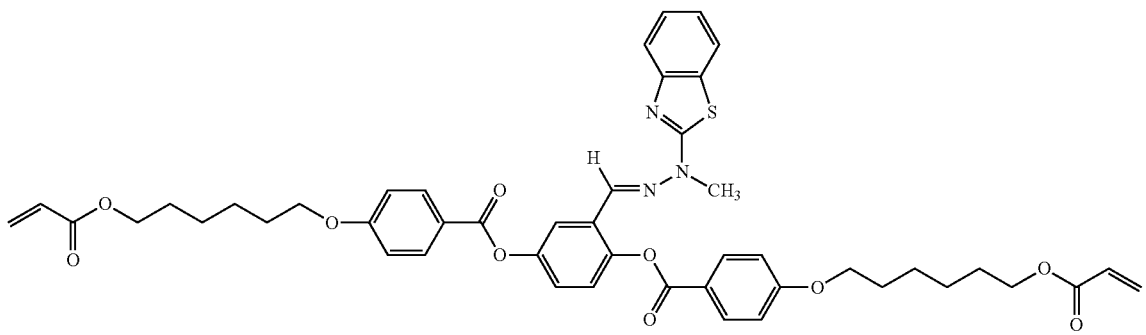

J=9.0 Hz), 7.01 (d, 2H, J=9.0 Hz), 6.41 (dd, 2H, J=1.5 Hz, 17.5 Hz), 6.14 (dd, 2H, J=10.5 Hz, 17.5 Hz), 5.83 (dd, 2H, J=1.5 Hz, 10.5 Hz), 4.194 (t, 2H, J=6.5 Hz), 4.192 (t, 2H, J=6.5 Hz), 4.08 (t, 4H, J=6.5 Hz), 3.63 (s, 3H), 1.84-1.89 (m, 4H), 1.71-1.77 (m, 4H), 1.46-1.59 (m, 8H)

Production Example 7

Synthesis of Polymerizable Compound 7

Polymerizable compound 7

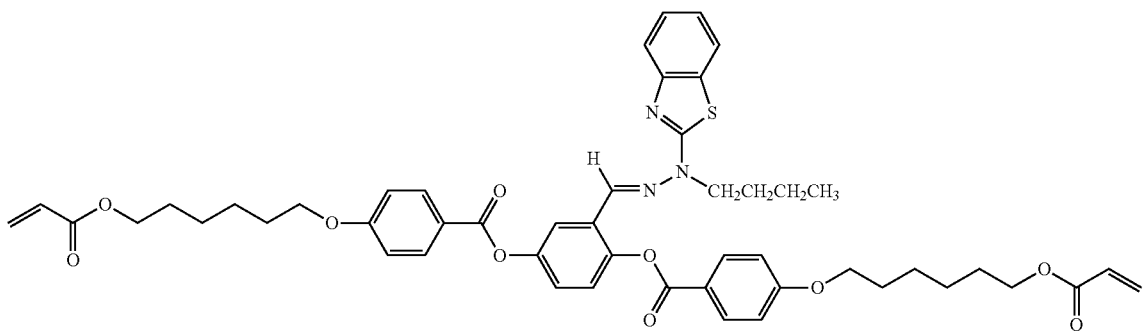

A four-necked reactor equipped with a thermometer was charged with 1.5 g (4.39 mmol) of the compound (I-7) synthesized in Example 7, 3.21 g (10.98 mmol) of 4-(6-acryloylhex-1-yloxy)benzoic acid (manufactured by DKSH Japan K.K.), 0.27 g (2.20 mmol) of 4-(dimethylamino)pyridine, and 100 ml of N-methylpyrrolidone under a nitrogen stream to prepare a homogeneous solution. After the addition of 2.53 g (13.18 mmol) of WSC to the solution, the mixture was stirred at 25° C. for 12 hours. After completion of the reaction, the reaction mixture was added to 800 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio)) to obtain 3.16 g of a polymerizable compound 7 as a light yellow solid (yield: 80.9%).

The structure of the target product was identified by $^1$H-NMR.

The $^1$H-NMR spectrum data are shown below.

$^1$H-NMR (500 MHz, CDCl$_3$, TMS, δ ppm): 8.20 (d, 2H, J=8.5 Hz), 8.19 (d, 2H, J=8.5 Hz), 7.90 (d, 1H, J=2.0 Hz), 7.76 (s, 1H), 7.61-7.64 (m, 2H), 7.25-7.32 (m, 3H), 7.12 (dd, 1H, J=7.5 Hz, 7.5 Hz), 7.01 (d, 4H, J=8.5 Hz), 6.41 (dd, 2H, J=1.5 Hz, 17.0 Hz), 6.14 (dd, 2H, J=10.5 Hz, 17.0 Hz), 5.83 (dd, 2H, J=1.5 Hz, 10.5 Hz), 4.17-4.21 (m, 6H), 4.08 (t, 2H, J=6.5 Hz), 4.07 (t, 2H, J=6.5 Hz), 1.84-1.91 (m, 4H), 1.71-1.77 (m, 4H), 1.46-1.61 (m, 10H), 1.19-1.28 (m, 2H), 0.77 (t, 3H, J=7.5 Hz.

Production Example 8

Synthesis of Polymerizable Compound 8

A four-necked reactor equipped with a thermometer was charged with 1.2 g (3.25 mmol) of the compound (I-8) synthesized in Example 8, 2.37 g (8.12 mmol) of 4-(6-acryloylhex-1-yloxy)benzoic acid (manufactured by DKSH Japan K.K.), 0.20 g (1.63 mmol) of 4-(dimethylamino)pyridine, and 100 ml of N-methylpyrrolidone under a nitrogen stream to prepare a homogeneous solution. After the addition of 1.87 g (9.74 mmol) of WSC to the solution, the mixture was stirred at 25° C. for 15 hours. After completion of the reaction, the reaction mixture was added to 800 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio)) to obtain 1.13 g of a polymerizable compound 8 as a light yellow solid (yield: 37.9%).

The structure of the target product was identified by $^1$H-NMR.

The $^1$H-NMR spectrum data are shown below.

$^1$H-NMR (500 MHz, CDCl$_3$, TMS, δ ppm): 8.20 (d, 2H, J=9.0 Hz), 8.19 (d, 2H, J=9.0 Hz), 7.90 (d, 1H, J=2.0 Hz), 7.76 (s, 1H), 7.63 (dd, 1H, J=1.0 Hz, 8.0 Hz), 7.62 (dd, 1H, J=1.0 Hz, 8.0 Hz), 7.25-7.34 (m, 3H), 7.12 (ddd, 1H, J=1.0 Hz, 7.5, 8.0 Hz), 7.01 (d, 2H, J=9.0 Hz), 7.00 (d, 2H, J=9.0 Hz), 6.42 (dd, 2H, J=1.5 Hz, 17.5 Hz), 6.14 (dd, 2H, J=10.0 Hz, 17.5 Hz), 5.83 (dd, 2H, J=1.5 Hz, 10.0 Hz), 6.16-4.21 (m, 6H), 4.08 (t, 2H, J=6.5 Hz), 4.06 (t, 2H, J=6.5 Hz), Polymerizable compound 8

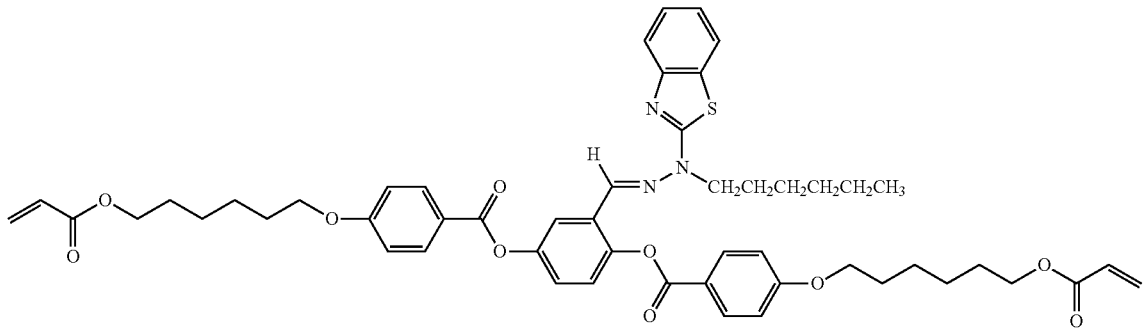

1.84-1.89 (m, 4H), 1.71-1.77 (m, 4H), 1.46-1.63 (m, 10H), 1.07-1.21 (m, 6H), 0.79 (t, 3H, J=6.5 Hz)

Production Example 9

Synthesis of Polymerizable Compound 9

Polymerizable compound 9

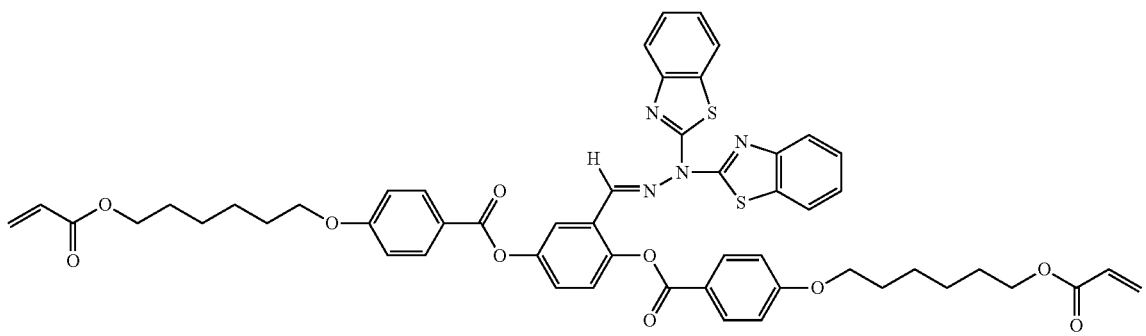

A four-necked reactor equipped with a thermometer was charged with 0.4 g (0.956 mmol) of the compound (I-9) synthesized in Example 9, 0.70 g (2.39 mmol) of 4-(6-acryloylhex-1-yloxy)benzoic acid (manufactured by DKSH Japan K.K.), 0.06 g (0.48 mmol) of 4-(dimethylamino) pyridine, and 50 ml of N-methylpyrrolidone under a nitrogen stream to prepare a homogeneous solution. After the addition of 0.55 g (2.87 mmol) of WSC to the solution, the mixture was stirred at 25° C. for 1.5 hours. After completion of the reaction, the reaction mixture was added to 500 ml of water, and extracted with 150 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio)) to obtain 0.64 g of a polymerizable compound 9 as a white solid (yield: 68.8%).

The structure of the target product was identified by $^1$H-NMR.

The $^1$H-NMR spectrum data are shown below.

$^1$H-NMR (400 MHz, THF-d$_8$, TMS, δ ppm): 10.84 (s, 1H), 8.24 (d, 2H, J=9.2 Hz), 8.17 (d, 2H, J=8.7 Hz), 8.06 (s, 1H), 7.85 (d, 2H, J=7.9 Hz), 7.44 (s, 2H), 7.39 (d, 2H, J=8.2 Hz), 7.23-7.31 (m, 4H), 7.07 (d, 2H, J=9.2 Hz), 7.06 (d, 2H, J=8.7 Hz), 6.32 (d, 2H, J=17.4 Hz), 6.10 (dd, 2H, J=10.1 Hz, 17.4 Hz), 5.77 (d, 2H, J=10.1 Hz), 4.08-4.16 (m, 8H), 1.80-1.90 (m, 4H), 1.66-1.75 (m, 4H), 1.43-1.61 (m, 8H)

Production Example 10

Synthesis of Polymerizable Compound 10

A four-necked reactor equipped with a thermometer was charged with 0.3 g (1.07 mmol) of the compound (I-10) synthesized in Example 10, 0.78 g (2.68 mmol) of 4-(6-acryloylhex-1-yloxy)benzoic acid (manufactured by DKSH Japan K.K.), 0.07 g (0.54 mmol) of 4-(dimethylamino) pyridine, and 50 ml of N-methylpyrrolidone under a nitrogen stream to prepare a homogeneous solution. After the addition of 0.62 g (3.21 mmol) of WSC to the solution, the mixture was stirred at 25° C. for 12 hours. After completion of the reaction, the reaction mixture was added to 500 ml of water, and extracted with 150 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio)) to obtain 336 mg of a polymerizable compound 10 as a yellow solid (yield: 37.9%).

The structure of the target product was identified by $^1$H-NMR.

The $^1$H-NMR spectrum data are shown below.

$^1$H-NMR (500 MHz, CDCl$_3$, TMS, δ ppm): 10.56 (s, 1H), 8.65 (s, 1H), 8.34 (d, 1H, J=7.5 Hz), 8.21 (d, 2H, J=9.0 Hz), 8.19 (d, 2H, J=9.0 Hz), 8.01 (d, 1H, J=2.5 Hz), 7.85 (s, 1H), 7.66 (dd, 1H, J=7.5 Hz, 7.5 Hz), 7.62 (dd, 1H, J=7.5 Hz, 7.5 Hz), 7.51 (d, 1H, J=7.5 Hz), 7.32 (dd, 1H, J=2.5 Hz, 8.5 Hz), 7.28 (d, 1H, J=8.5 Hz), 7.00 (d, 2H, J=9.0 Hz), 6.99 (d, 2H, J=9.0 Hz), 6.41 (dd, 2H, J=1.5 Hz, 17.5 Hz), 6.13 (dd, 2H, J=10.5 Hz, 17.5 Hz), 5.83 (dd, 2H, J=1.5 Hz, 10.5 Hz), 4.20 (t, 2H, J=6.5 Hz), 4.19 (t, 2H, J=7.0 Hz), 4.08 (t, 2H, J=6.5 Hz), 4.07 (t, 2H, J=6.5 Hz), 1.83-1.89 (m, 4H), 1.71-1.77 (m, 4H), 1.45-1.59 (m, 8H)

Polymerizable compound 10

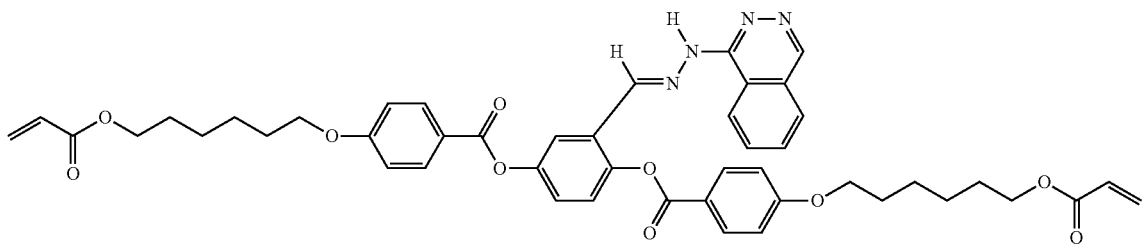

Production Example 11

Synthesis of Polymerizable Compound 11

Polymerizable compound 11

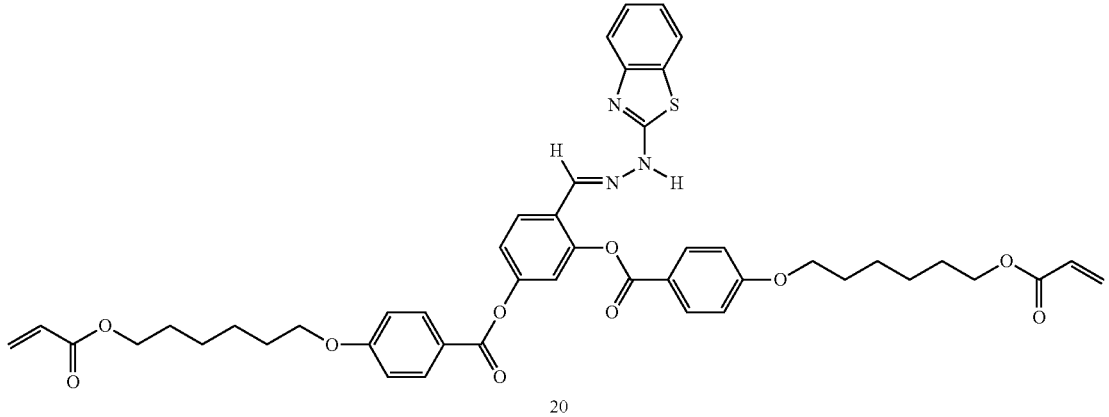

A four-necked reactor equipped with a thermometer was charged with 3.0 g (10.51 mmol) of the compound 1r synthesized in Reference Example 1, 7.68 g (26.29 mmol) of 4-(6-acryloylhex-1-yloxy)benzoic acid (manufactured by DKSH Japan K.K.), 0.64 g (5.26 mmol) of 4-(dimethylamino)pyridine, and 200 ml of N-methylpyrrolidone under a nitrogen stream to prepare a homogeneous solution. After the addition of 6.05 g (31.54 mmol) of WSC to the solution, the mixture was stirred at 5° C. for 12 hours. After completion of the reaction, the reaction mixture was added to 1 l of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=8:2 (volume ratio)) to obtain 5.1 g of a polymerizable compound 11 as a light yellow solid (yield: 58.2%).

The structure of the target product was identified by $^1$H-NMR.

The $^1$H-NMR spectrum data are shown below.

$^1$H-NMR (400 MHz, DMSO-$d_6$, TMS, δ ppm): 12.38 (brs, 1H), 8.16 (s, 1H), 7.89 (d, 2H, J=8.7 Hz), 7.87 (d, 2H, J=8.7 Hz), 7.67-7.74 (m, 3H), 7.51 (d, 1H, J=7.8 Hz), 7.41 (brs, 1H), 7.26 (dd, 1H, J=7.8 Hz, 7.8 Hz), 7.07 (dd, 1H, J=7.8 Hz, 7.8 Hz), 6.95 (d, 2H, J=8.2 Hz), 6.94 (d, 2H, J=8.2 Hz), 6.27 (dd, 2H, J=1.4 Hz, 17.4 Hz), 6.12 (dd, 2H, J=10.1 Hz, 17.4 Hz), 5.87 (dd, 2H, J=1.4 Hz, 10.1 Hz), 4.06 (t, 4H, J=6.6 Hz), 3.96-4.00 (m, 4H), 1.64-1.69 (m, 4H), 1.55-1.62 (m, 4H), 1.33-1.42 (m, 8H)

Production Example 12

Synthesis of Polymerizable Compound 12

Polymerizable compound 12

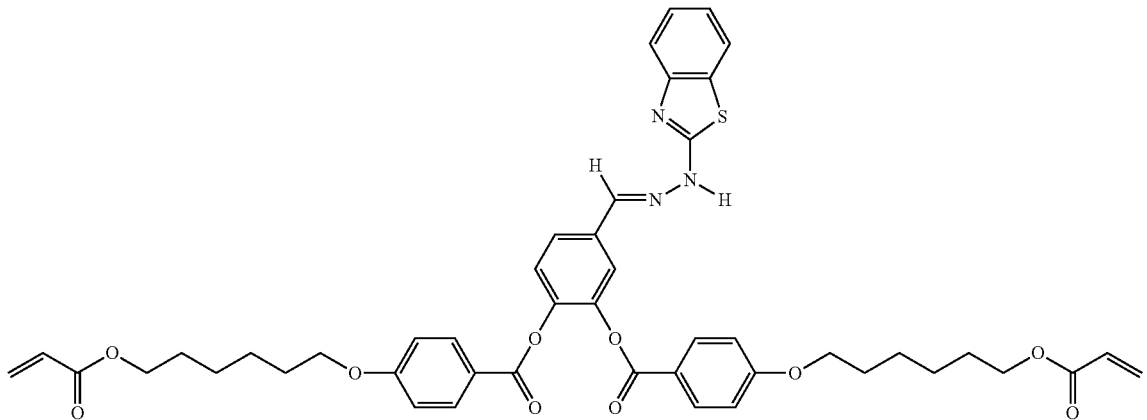

A four-necked reactor equipped with a thermometer was charged with 3.0 g (10.51 mmol) of the compound 2r synthesized in Reference Example 2, 7.68 g (26.29 mmol) of 4-(6-acryloylhex-1-yloxy)benzoic acid (manufactured by DKSH Japan K.K.), 0.64 g (5.26 mmol) of 4-(dimethylamino)pyridine, and 200 ml of N-methylpyrrolidone under a nitrogen stream to prepare a homogeneous solution. After the addition of 6.05 g (31.54 mmol) of WSC to the solution, the mixture was stirred at 25° C. for 12 hours. After completion of the reaction, the reaction mixture was added to 1 l of water, and extracted with 500 ml of ethyl acetate. After drying the ethyl acetate layer over anhydrous sodium sulfate, sodium sulfate was filtered off Ethyl acetate was evaporated from the filtrate under reduced pressure using a rotary evaporator to obtain a light yellow solid. The light yellow solid was purified by silica gel column chromatography (toluene:ethyl acetate=8:2 (volume ratio)) to obtain 6.80 g of a polymerizable compound 12 as a light yellow solid (yield: 77.5%).

The structure of the target product was identified by $^1$H-NMR.

The $^1$H-NMR spectrum data are shown below.

$^1$H-NMR (400 MHz, DMSO-$d_6$, TMS, δ ppm): 12.23 (brs, 1H), 8.17 (s, 1H), 8.10 (d, 2H, J=8.7 Hz), 8.04 (d, 2H, J=8.7 Hz), 7.97 (d, 1H, 8.7 Hz), 7.67 (d, 1H, J=7.8 Hz), 7.31-7.40 (m, 3H), 7.25 (dd, 1H, J=7.8 Hz, 7.8 Hz), 7.05-7.14 (m, 5H), 6.29 (dd, 2H, J=1.4 Hz, 17.4 Hz), 6.14 (dd, 2H, J=10.6 Hz, 17.4 Hz), 5.90 (dd, 2H, J=1.4 Hz, 10.6 Hz), 4.09-4.10 (m, 8H), 1.68-1.78 (m, 4H), 1.57-1.65 (m, 4H), 1.35-1.47 (m, 8H)

Production Example 13

Synthesis of Polymerizable Compound 13

A four-necked reactor equipped with a thermometer was charged with 1.90 g (5.19 mmol) of the compound (I-11) synthesized in Example 11, 3.79 g (13.0 mmol) of 4-(6-acryloylhex-1-yloxy)benzoic acid (manufactured by DKSH Japan K.K.), 318 mg (2.60 mmol) of 4-(dimethylamino) pyridine, and 20 ml of N-methylpyrrolidone under a nitrogen stream to prepare a homogeneous solution. After the addition of 2.98 g (15.6 mmol) of WSC to the solution, the mixture was stirred at room temperature for 16 hours. After completion of the reaction, the reaction mixture was added to 300 ml of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene:ethyl acetate=95:5 (volume ratio)) to obtain 1.92 g of a polymerizable compound 13 as a white solid (yield: 40.4%).

The structure of the target product was identified by $^1$H-NMR.

The $^1$H-NMR spectrum data are shown below.

$^1$H-NMR (400 MHz, CDCl$_3$, TMS, δ ppm): 8.19 (d, 4H, J=8.2 Hz), 7.88 (s, 1H), 7.73 (s, 1H), 7.61 (d, 1H, J=7.8 Hz), 7.60 (d, 1H, J=6.9 Hz), 7.27-7.33 (m, 3H), 7.13 (dd, 1H, J=7.3, 7.8 Hz), 7.03 (d, 2H, J=8.7 Hz), 6.99 (d, 2H, J=9.2 Hz), 6.41 (dd, 2H, J=1.4 Hz, 17.4 Hz), 6.13 (dd, 2H, J=10.5 Hz, 17.4 Hz), 5.82 (dd, 2H, J=1.4 Hz, 10.5 Hz), 4.27 (t, 2H, J=6.9 Hz), 4.19 (t, 2H, J=6.6 Hz), 4.18 (t, 2H, J=6.6 Hz), 4.08 (t, 2H, J=6.0 Hz), 4.07 (t, 2H, J=6.4 Hz), 2.30 (t, 2H, J=7.1 Hz), 1.82-1.89 (m, 4H), 1.70-1.78 (m, 6H), 1.45-1.60 (m, 10H)

Polymerizable compound 13

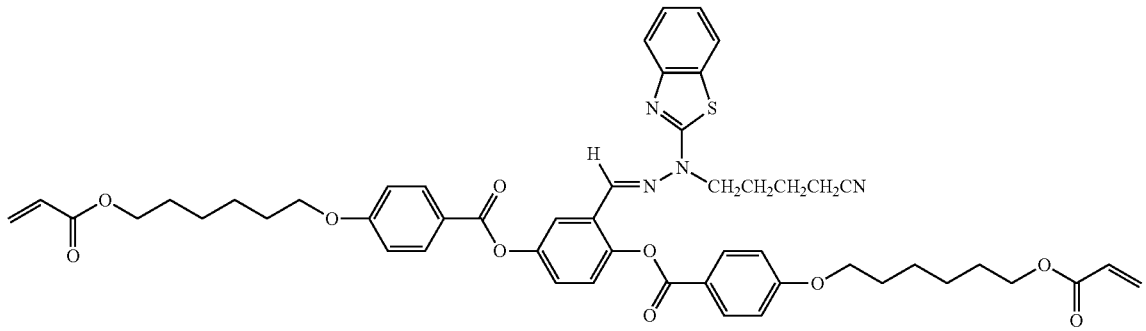

Production Example 14

Synthesis of Polymerizable Compound 14

Polymerizable compound 14

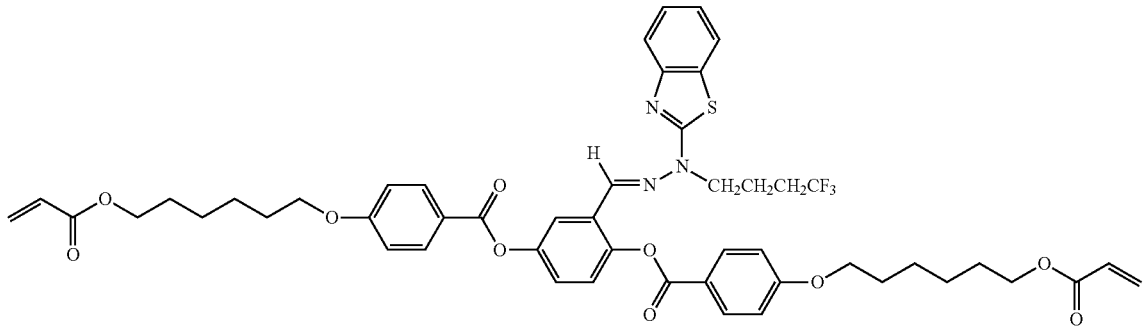

A four-necked reactor equipped with a thermometer was charged with 575 mg (1.45 mmol) of the compound (I-12) synthesized in Example 12, 1.06 g (3.64 mmol) of 4-(6-acryloylhex-1-yloxy)benzoic acid (manufactured by DKSH Japan K.K.), 88.6 mg (0.73 mmol) of 4-(dimethylamino)pyridine, and 10 ml of N-methylpyrrolidone under a nitrogen stream to prepare a homogeneous solution. After the addition of 834 mg (4.35 mmol) of WSC to the solution, the mixture was stirred at room temperature for 16 hours. After completion of the reaction, the reaction mixture was added to 150 ml of water, and extracted with 200 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene:ethyl acetate=95:5 (volume ratio)) to obtain 1.13 g of a polymerizable compound 14 as a white solid (yield: 82.6%).

The structure of the target product was identified by $^1$H-NMR.

The $^1$H-NMR spectrum data are shown below.

$^1$H-NMR (500 MHz, CDCl$_3$, TMS, δ ppm): 8.20 (d, 2H, J=8.5 Hz), 8.18 (d, 2H, J=8.5 Hz), 7.90 (d, 1H, J=2.9 Hz), 7.75 (s, 1H), 7.62-7.66 (m, 2H), 7.27-7.34 (m, 3H), 7.15 (dd, 1H, J=7.5 Hz, 7.5 Hz), 7.01 (d, 4H, J=8.5 Hz), 6.41 (dd, 2H, J=1.5 Hz, 17.5 Hz), 6.14 (dd, 2H, J=10.5 Hz, 17.5 Hz), 5.83 (d, 2H, J=1.5 Hz, 10.5 Hz), 4.28 (t, 2H, J=7.0 Hz), 4.194 (t, 2H, J=6.5 Hz), 4.191 (t, 2H, J=6.5 Hz), 4.08 (t, 2H, J=6.5 Hz), 4.07 (t, 2H, J=6.5 Hz), 2.01-2.12 (m, 2H), 1.83 (t, 6H), 1.71-1.77 (m, 4H) 1.45-1.59 (m, 8H)

Production Example 15

Synthesis of Polymerizable Compound 15

A four-necked reactor equipped with a thermometer was charged with 560 mg (1.65 mmol) of the compound (I-13) synthesized in Example 13, 1.21 g (4.13 mmol) of 4-(6-acryloylhex-1-yloxy)benzoic acid (manufactured by DKSH Japan K.K.), 100.8 mg (0.825 mmol) of 4-(dimethylamino)pyridine, and 20 ml of N-methylpyrrolidone under a nitrogen stream to prepare a homogeneous solution. After the addition of 948 mg (4.95 mmol) of WSC to the solution, the mixture was stirred at room temperature for 16 hours. After completion of the reaction, the reaction mixture was added to 200 ml of water, and extracted with 250 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene:ethyl acetate=90:10 (volume ratio)) to obtain 1.09 g of a polymerizable compound 15 as a white solid (yield: 74.4%).

The structure of the target product was identified by $^1$H-NMR.

The $^1$H-NMR spectrum data are shown below.

$^1$H-NMR (500 MHz, CDCl$_3$, TMS, δ ppm): 8.21 (d, 2H, J=9.0 Hz), 8.19 (d, 2H, J=9.0 Hz), 7.90 (d, 1H, J=2.0 Hz), 7.80 (s, 1H), 7.64 (d, 1H, J=7.3 Hz), 7.63 (d, 1H, J=8.0 Hz), 7.28-7.33 (m, 3H), 7.13 (dd, 1H, J=7.3 Hz, 7.8 Hz), 7.01 (d, 4H, J=9.0 Hz), 6.42 (dd, 2H, J=1.5 Hz, 17.5 Hz), 6.14 (dd, 2H, J=10.5 Hz, 17.5 Hz), 5.83 (dd, 2H, J=1.5 Hz, 10.5 Hz), 5.62-5.70 (m, 1H), 4.86-4.90 (m, 2H), 4.26 (t, 2H, J=7.0 Hz), 4.20 (t, 4H, J=6.5 Hz), 4.080 (t, 2H, J=6.0 Hz), 4.076 (t, 2H, J=6.0 Hz), 2.39 (dt, 2H, J=7.5 Hz, 7.5 Hz), 1.84-1.90 (m, 4H), 1.72-1.77 (m, 4H), 1.46-1.59 (m, 8H)

Polymerizable compound 15

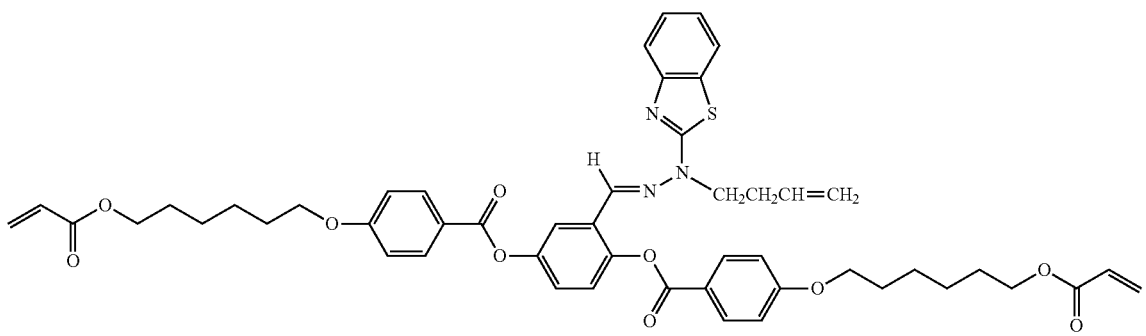

Production Example 16

Synthesis of Polymerizable Compound 16

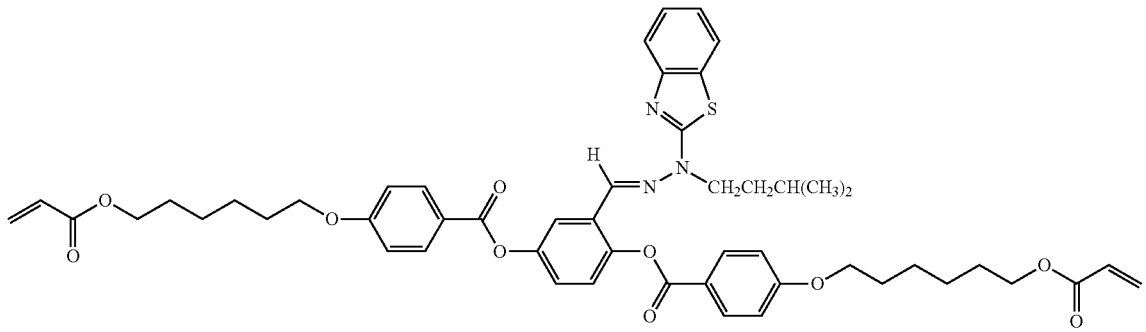

Polymerizable compound 16

A four-necked reactor equipped with a thermometer was charged with 1.36 g (3.83 mmol) of the compound (I-14) synthesized in Example 14, 2.80 g (9.58 mmol) of 4-(6-acryloylhex-1-yloxy)benzoic acid (manufactured by DKSH Japan K.K.), 234 mg (1.92 mmol) of 4-(dimethylamino)pyridine, and 20 ml of N-methylpyrrolidone under a nitrogen stream to prepare a homogeneous solution. After the addition of 2.20 g (11.5 mmol) of WSC to the solution, the mixture was stirred at room temperature for 5 hours. After completion of the reaction, the reaction mixture was added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene:ethyl acetate=90:10 (volume ratio)) to obtain 1.61 g of a polymerizable compound 16 as a white solid (yield: 46.5%).

The structure of the target product was identified by $^1$H-NMR.

The $^1$H-NMR spectrum data are shown below.

$^1$H-NMR (500 MHz, CDCl$_3$, TMS, δ ppm): 8.21 (d, 2H, J=9.0 Hz), 8.19 (d, 2H, J=9.0 Hz), 7.90 (s, 1H), 7.76 (s, 1H), 7.61-7.64 (m, 2H), 7.30 (dd, 1H, J=7.5 Hz, 8.0 Hz), 7.24-7.27 (m, 2H), 7.12 (dd, 1H, J=7.5 Hz, 8.0 Hz), 7.01 (d, 2H, J=9.0 Hz), 7.00 (d, 2H, J=9.0 Hz), 6.42 (dd, 2H, J=1.5 Hz, 17.5 Hz), 6.14 (dd, 2H, J=10.5 Hz, 17, 5 Hz), 5.83 (dd, 2H, J=1.5 Hz, 10.5 Hz), 4.18-4.22 (m, 6H), 4.08 (t, 2H, J=6.5 Hz), 4.07 (t, 2H, J=6.5 Hz), 1.84-1.89 (m, 4H), 1.70-1.77 (m, 4H), 1.48-1.59 (m, 11H), 0.78 (d, 6H, J=6.0 Hz)

Production Example 17

Synthesis of Polymerizable Compound 17

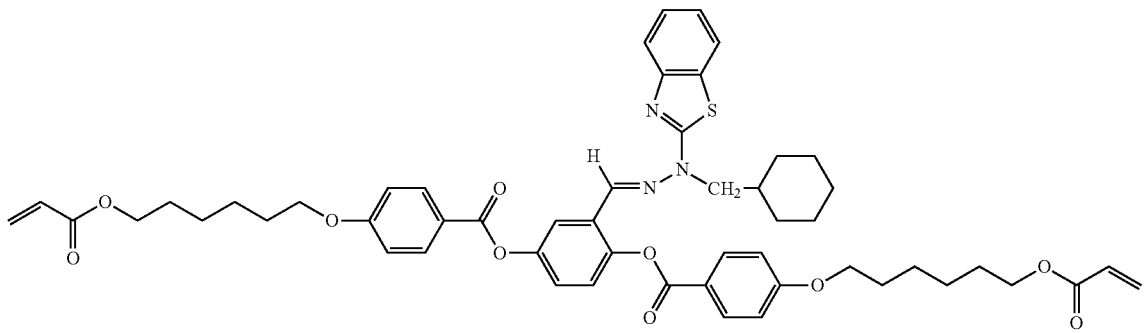

Polymerizable compound 17

A four-necked reactor equipped with a thermometer was charged with 2.00 g (5.42 mmol) of the compound (I-15) synthesized in Example 15, 3.83 g (13.1 mmol) of 4-(6-acryloylhex-1-yloxy)benzoic acid (manufactured by DKSH Japan K.K.), 320 mg (2.62 mmol) of 4-(dimethylamino)pyridine, and 20 ml of N-methylpyrrolidone under a nitrogen stream to prepare a homogeneous solution. After the addition of 3.01 g (15.7 mmol) of WSC to the solution, the mixture was stirred at room temperature for 16 hours. After completion of the reaction, the reaction mixture was added to 300 ml of water, and extracted with 500 ml of ethyl acetate. After drying the ethyl acetate layer over anhydrous sodium sulfate, sodium sulfate was filtered off Ethyl acetate was evaporated from the filtrate under reduced pressure using a rotary evaporator to obtain a white solid. The white solid was purified by silica gel column chromatography (toluene:ethyl acetate=95:5 (volume ratio)) to obtain 2.68 g of a polymerizable compound 17 as a white solid (yield: 55.0%).

The structure of the target product was identified by $^1$H-NMR.

The $^1$H-NMR spectrum data are shown below.

¹H-NMR (500 MHz, CDCl₃, TMS, δ ppm): 8.20 (d, 2H, J=8.7 Hz), 8.18 (d, 2H, J=8.7 Hz), 7.89 (d, 1H, J=2.9 Hz), 7.76 (s, 1H), 7.61 (d, 2H, J=8.2 Hz), 7.24-7.30 (m, 3H), 7.11 (dd, 1H, J=7.3 Hz, 7.8 Hz), 7.00 (d, 4H, J=8.7 Hz), 6.41 (d, 2H, J=17.4 Hz), 6.13 (dd, 2H, J=10.5 Hz, 17.4 Hz), 5.82 (d, 2H, J=10.5 Hz), 4.19 (t, 4H, J=6.4 Hz), 4.04-4.08 (m, 6H), 1.82-1.89 (m, 4H), 1.70-1.77 (m, 5H), 1.48-1.59 (m, 13H), 0.96-1.03 (m, 5H)

Production Example 18

Synthesis of Polymerizable Compound 18

The ¹H-NMR spectrum data are shown below.

¹H-NMR (500 MHz, CDCl₃, TMS, δ ppm): 8.28 (s, 1H), 8.21 (d, 2H, J=9.0 Hz), 8.20 (d, 2H, J=9.0 Hz), 7.87 (d, 1H, J=2.5 Hz), 7.62 (d, 1H, J=7.5 Hz), 7.56 (d, 1H, J=8.0 Hz), 7.31 (d, 1H, J=8.5 Hz), 7.25-7.29 (m, 2H), 7.11 (dd, 1H, J=7.5 Hz, 8.0 Hz), 7.012 (d, 2H, J=9.0 Hz), 7.008 (d, 2H, J=9.0 Hz), 6.41 (dd, 2H, J=1.5 Hz, 17.5 Hz), 6.13 (dd, 2H, J=10.5 Hz, 17, 5 Hz), 5, 83 (dd, 2H, J=1.5 Hz, 10.5 Hz), 4.74 (tt, 1H, J=4.0 Hz, 12.5 Hz), 4.19 (t, 4H, J=7.0 Hz), 4.08 (t, 2H, J=6.5 Hz), 4.07 (t, 2H, J=6.5 Hz), 2.14-2.22 (m, 2H), 1.84-1.89 (m, 6H), 1.71-1.77 (m, 6H), 1.44-1.59 (m, 9H), 1.26-1.34 (m, 2H), 0.72-0.80 (m, 1H)

Polymerizable compound 18

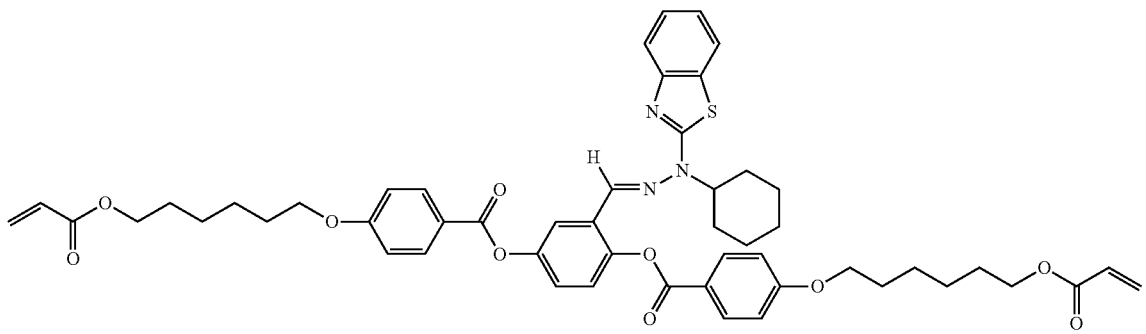

A four-necked reactor equipped with a thermometer was charged with 685 mg (1.73 mmol) of the compound (I-16) synthesized in Example 16, 1.27 g (4.33 mmol) of 4-(6-acryloylhex-1-yloxy)benzoic acid (manufactured by DKSH Japan K.K.), 106 mg (0.865 mmol) of 4-(dimethylamino) pyridine, and 10 ml of N-methylpyrrolidone under a nitrogen stream to prepare a homogeneous solution. After the addition of 995 mg (5.19 mmol) of WSC to the solution, the mixture was stirred at room temperature for 18 hours. After completion of the reaction, the reaction mixture was added to 100 ml of water, and extracted with 200 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a white solid. The white solid was purified by silica gel column chromatography (toluene:ethyl acetate=90:10 (volume ratio)) to obtain 1.17 g of a polymerizable compound 18 as a white solid (yield: 73.8%).

The structure of the target product was identified by ¹H-NMR.

The phase transition temperature was evaluated, the retardation was measured, and the wavelength dispersion was evaluated using the polymerizable compounds 1 to 18 obtained in Production Examples 1 to 18.

Measurement of Phase Transition Temperature 10 mg of the polymerizable compound (polymerizable compounds 1 to 18) was weighed, and placed in a solid state between two glass substrates provided with a polyimide alignment film subjected to a rubbing treatment. The substrates were placed on a hot plate, heated from 50° C. to 200° C., and cooled to 50° C. A change in structure during a change in temperature was observed using a polarizing optical microscope ("ECLIPSE LV100POL" manufactured by Nikon Corporation).

The phase transition temperature measurement results are shown in Table 2.

In Table 2, "C" indicates "crystal", "N" indicates "nematic", and "I" indicates "isotropic". The term "crystal" means that the test compound was in a solid phase, the term "nematic" means that the test compound was in a nematic liquid crystal phase, and the term "isotropic" means that the test compound was in an isotropic liquid phase.

TABLE 2

| | Intermediate | Polymerizable compound | Phase transition temperature | | | | | Liquid crystal phase temperature range | Liquid crystal-linity |
|---|---|---|---|---|---|---|---|---|---|
| Production Example 1 | Compound (I-1) | 1 | C | 102° C. ⇄ 50° C. or less | N | 165° C. ⇄ 140° C. | I | 90° C. or more | Present |
| Production Example 2 | Compound (I-2) | 2 | C | 150° C. ⇄ 113° C. | N | 155° C. ⇄ 150° C. | I | 37° C. | Present |
| Production Example 3 | Compound (I-3) | 3 | C | 119° C. ⇄ 50° C. or less | N | 70° C. | I | 20° C. or more | Present |
| Production Example 4 | Compound (I-4) | 4 | C | 85° C. ⇄ 50° C. or less | N | 75° C. | I | 25° C. or more | Present |
| Production Example 5 | Compound (I-5) | 5 | C | 90° C. ⇄ 50° C. or less | N | 112° C. ⇄ 111° C. | I | 61° C. or more | Present |
| Production Example 6 | Compound (I-6) | 6 | C | 107° C. ⇄ 50° C. or less | N | 94° C. | I | 44° C. or more | Present |
| Production Example 7 | Compound (I-7) | 7 | C | 97° C. ⇄ 50° C. or less | N | 77° C. | I | 22° C. or more | Present |
| Production Example 8 | Compound (I-8) | 8 | C | 83° C. ⇄ 50° C. or less | N | 85° C. ⇄ 82° C. | I | 32° C. or more | Present |
| Production Example 9 | Compound (I-9) | 9 | C | 160° C. ⇄ 112° C. | N | 168° C. ⇄ 163° C. | I | 51° C. | Present |
| Production Example 10 | Compound (I-10) | 10 | C | 116° C. ⇄ 50° C. or less | N | 127° C. ⇄ 120° C. | I | 70° C. or more | Present |
| Production Example 11 | Compound 1r | 11 | C | 128° C. ⇄ Not observed due to thermal polymerization | | | I | — | Absent |
| Production Example 12 | Compound 2r | 12 | C | 125° C. ⇄ 91° C. | | | I | — | Absent |
| Production Example 13 | Compound (I-11) | 13 | C | 115° C. ⇄ 50° C. or less | N | 79° C. | I | 29° C. or more | Present |

TABLE 2-continued

| | Intermediate | Polymerizable compound | Phase transition temperature | | Liquid crystal phase temperature range | Liquid crystal-linity |
|---|---|---|---|---|---|---|
| Production Example 14 | Compound (I-12) | 14 | C ⇌ 50° C. or less  111° C. / 58° C. N ⇌ | I | 8° C. or more | Present |
| Production Example 15 | Compound (I-13) | 15 | C ⇌ 80° C. 112° C. / 87° C. N ⇌ | I | 7° C. | Present |
| Production Example 16 | Compound (I-14) | 16 | C ⇌ 50° C. or less 98° C. / 72° C. N ⇌ | I | 22° C. or more | Present |
| Production Example 17 | Compound (I-15) | 17 | C ⇌ 50° C. or less 120° C. / 66° C. N ⇌ | I | 16° C. or more | Present |
| Production Example 18 | Compound (I-16) | 18 | C ⇌ 50° C. or less 94° C. / 100° C. N ⇌ 105° C. | I | 50° C. or more | Present |

As shown in Table 2, while the polymerizable compounds 1 to 10 and 13 to 18 of Production Examples 1 to 10 and 13 to 18 produced using the compounds (I-1) to (I-16) obtained in Examples 1 to 16 exhibited liquid crystallinity, the polymerizable compounds 11 and 12 produced using the compounds 1r and 2r obtained in Reference Examples 1r and 2r did not exhibit liquid crystallinity.

Measurement of Wavelength Dispersion
(1) Preparation of Polymerizable Composition 1 g of the polymerizable compound (polymerizable compounds 1 to 18 obtained in Production Examples 1 to 18), 30 mg of Adekaoptomer N-1919 (manufactured by Adeka Corporation) (photoinitiator), and 100 mg of a 1% cyclopentanone solution of KH-40 (manufactured by AGC Seimi Chemical Co., Ltd.) (surfactant) were dissolved in 2.3 g of cyclopentanone. The solution was filtered through a disposable filter having a pore size of 0.45 micrometers to obtain a polymerizable composition (polymerizable compositions 1 to 18).

(2) Measurement of Retardation and Evaluation of Wavelength Dispersion
(i) Preparation of Transparent Resin Substrate Provided with Alignment Film Each side of an alicyclic olefin polymer film ("ZeonorFilm ZF16-100" manufactured by Zeon Corporation) (thickness: 100 micrometers) was subjected to a corona discharge treatment. A 5% polyvinyl alcohol aqueous solution was applied to one side of the film using a #2 wire bar, and the film was dried to form an alignment film having a thickness of 0.1 micrometers. The alignment film was subjected to a rubbing treatment to prepare a transparent resin substrate on which the alignment film was formed.

(ii) Formation of Liquid Crystal Layer Using Polymerizable Composition

Each polymerizable composition (polymerizable compositions 1 to 18) was applied to the surface of the transparent resin substrate on which the alignment film was formed, using a #4 wire bar. The film was dried for 30 seconds at the temperature shown in Table 3, and subjected to an alignment treatment for 1 minute at the temperature shown in Table 3 to form a liquid crystal layer. UV rays were applied to the liquid crystal layer at a dose of 2000 mJ/cm² to effect polymerization to prepare a wavelength dispersion measurement sample.

(iii) Measurement of Retardation

The retardation between 400 nm and 800 nm was measured using the sample utilizing an ellipsometer ("XLS-100" manufactured by J. A. Woollam).

(iv) Evaluation of Wavelength Dispersion

The wavelength dispersion was evaluated from the values α and β calculated by the following expressions using the measured retardation.

$$\alpha = (\text{retardation at 449.9 nm})/(\text{retardation at 548.5 nm})$$

$$\beta = (\text{retardation at 650.2 nm})/(\text{retardation at 548.5 nm})$$

The value α is smaller than 1, and the value β is larger than 1 when ideal wideband wavelength dispersion (reverse wavelength dispersion) is achieved. The values α and β are almost identical when flat wavelength dispersion is achieved. The value α is larger than 1, and the value β is smaller than 1 when normal dispersion is achieved.

Specifically, flat wavelength dispersion that ensures that the values α and β are almost identical is preferable, and reverse wavelength dispersion that ensures that the value α is smaller than 1, and the value β is larger than 1, is particularly preferable.

Table 3 shows the film drying temperature, the alignment treatment temperature, the thickness (micrometers) of the liquid crystal polymer films obtained by polymerizing the polymerizable compositions 1 to 18, the retardation (Re) at a wavelength of 548.5 nm, and the values α and β.

TABLE 3

| | Intermediate | Polymerizable compound | Polymerizable composition | Drying temperature (° C.) | Alignment treatment temperature(° C.) | Re (548.5 nm) | α | β | Thickness (micrometers) |
|---|---|---|---|---|---|---|---|---|---|
| Production Example 1 | Compound (I-1) | 1 | 1 | 110 | 23 | 129.59 | 0.902 | 1.012 | 1.350 |
| Production Example 2 | Compound (I-2) | 2 | 2 | 158 | 125 | 126.04 | 1.011 | 0.999 | 1.478 |
| Production Example 3 | Compound (I-3) | 3 | 3 | 125 | 65 | 149.70 | 0.905 | 0.976 | 1.421 |
| Production Example 4 | Compound (I-4) | 4 | 4 | 90 | 65 | 131.02 | 1.005 | 0.985 | 1.565 |
| Production Example 5 | Compound (I-5) | 5 | 5 | 100 | 23 | 163.78 | 0.914 | 1.026 | 1.574 |
| Production Example 6 | Compound (I-6) | 6 | 6 | 110 | 23 | 164.16 | 0.949 | 0.982 | 1.598 |
| Production Example 7 | Compound (I-7) | 7 | 7 | 110 | 23 | 146.90 | 0.946 | 1.002 | 1.577 |
| Production Example 8 | Compound (I-8) | 8 | 8 | 100 | 23 | 151.10 | 0.932 | 1.004 | 1.434 |
| Production Example 9 | Compound (I-9) | 9 | 9 | 170 | 125 | 142.53 | 0.986 | 0.988 | 1.353 |
| Production Example 10 | Compound (I-10) | 10 | 10 | 135 | 23 | 127.53 | 0.047 | 1.075 | 1.588 |
| Production Example 11 | Compound 1r | 11 | 11 | N.A. | N.A. | N.A. | N.A. | N.A. | N.A. |
| Production Example 12 | Compound 2r | 12 | 12 | N.A. | N.A. | N.A. | N.A. | N.A. | N.A. |
| Production Example 13 | Compound (I-11) | 13 | 13 | 125 | 60 | 144.16 | 0.946 | 1.013 | 1.558 |
| Production Example 14 | Compound (I-12) | 14 | 14 | 120 | 50 | 109.51 | 0.947 | 0.972 | 1.470 |
| Production Example 15 | Compound (I-13) | 15 | 15 | 120 | 83 | 142.65 | 0.915 | 1.011 | 1.514 |
| Production Example 16 | Compound (I-14) | 16 | 16 | 100 | 23 | 137.60 | 0.900 | 0.993 | 1.573 |
| Production Example 17 | Compound (I-15) | 17 | 17 | 125 | 60 | 132.10 | 0.941 | 1.001 | 1.575 |
| Production Example 18 | Compound (I-16) | 18 | 18 | 110 | 23 | 146.46 | 0.934 | 0.981 | 1.583 |

The invention claimed is:

1. A compound represented by a formula (I),

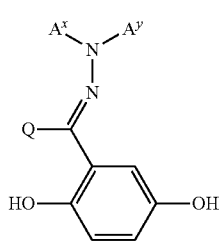

(I)

wherein $A^x$ is an organic group having 2 to 30 carbon atoms that includes at least one aromatic ring selected from the group consisting of an anthracene ring, a fluorene ring, a pyridazine ring, a benzothiophene ring, a benzofuran ring, a benzoxazole ring, a phthalazine ring, and a carbazole ring, $A^y$ is a hydrogen atom, a substituted or unsubstituted alkyl group having 1 to 18 carbon atoms, a substituted or unsubstituted cycloalkyl group, a substituted or unsubstituted alkenyl group having 2 to 18 carbon atoms, or an organic group having 2 to 30 carbon atoms that includes at least one aromatic ring selected from the group consisting of an aromatic hydrocarbon ring and an aromatic hetero ring, provided that the aromatic ring included in $A^x$ and $A^y$ is substituted or unsubstituted, and $A^x$ and $A^y$ optionally bond to each other to form a ring, and Q is a hydrogen atom.

2. The compound according to claim 1, wherein a total number of aromatic ring π-electrons included in $A^x$ and $A^y$ is 24 or less.

3. The compound according to claim 1, wherein $A^y$ is a hydrogen atom, or a substituted or unsubstituted alkyl group having 1 to 6 carbon atoms.

4. A method for producing a hydrazone compound represented by a formula (I), the method comprising reacting a carbonyl compound represented by a formula (II) with a hydrazine compound represented by a formula (III) in a solvent,

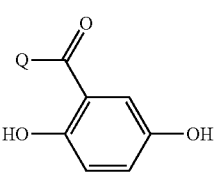

(II)

wherein Q is a hydrogen atom,

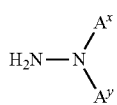

(III)

wherein $A^x$ is an organic group having 2 to 30 carbon atoms that includes at least one aromatic ring selected from the group consisting of an anthracene ring, a fluorene ring, a pyridazine ring, a benzothiophene ring, a benzofuran ring, a benzoxazole ring, a phthalazine ring, and a carbazole ring, $A^y$ is a hydrogen atom, a substituted or unsubstituted alkyl group having 1 to 18 carbon atoms, a substituted or unsubstituted cycloalkyl group, a substituted or unsubstituted alkenyl group having 2 to 18 carbon atoms, or an organic group having 2 to 30 carbon atoms that includes at least one aromatic ring selected from the group consisting of an aromatic hydrocarbon ring and an aromatic hetero ring, provided that the aromatic ring included in $A^x$ and $A^y$ is substituted or unsubstituted, and $A^x$ and $A^y$ optionally bond to each other to form a ring,

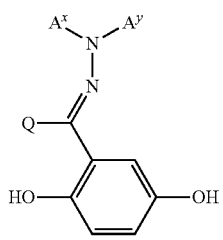

(I)

wherein Q, $A^x$, and $A^y$ are the same as defined above.

5. The method according to claim 4, wherein the solvent is an alcohol-based solvent.

6. The method according to claim 5, wherein the alcohol-based solvent is an alcohol-based solvent having 1 to 4 carbon atoms.

7. The compound according to claim 2, wherein $A^y$ is a hydrogen atom, or a substituted or unsubstituted alkyl group having 1 to 6 carbon atoms.

8. A compound represented by a formula (I),

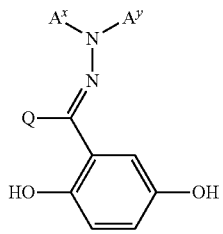

(I)

wherein $A^x$ is an aromatic group selected from the group consisting of a naphthalene group, an anthracene group, a fluorene group, a pyrrole group, a furan group, a thiophene group, a pyrazole group, an imidazole group, an oxazole group, a thiazole group, a pyridine group, a pyridazine group, a pyrimidine group, a pyrazine group, a benzimidazole group, a benzothiophene group, a benzofuran group, a benzothiazole group, a benzoxazole group, a quinoline group, a phthalazine group, and a carbazole group, wherein the naphthalene group, the anthracene group, the fluorene group, the pyrrole group, the furan group, the thiophene group, the pyrazole group, the imidazole group, the thiazole group, the pyridine group, the pyridazine group, the pyrimidine group, the pyrazine group, the benzimidazole group, the benzothiophene group, the benzofuran group, the benzothiazole group, the benzoxazole group, the phthalazine group, and the carbazole group are optionally substituted with one substituent or a plurality of identical or different substituents selected from a halogen atom, a cyano group, an alkyl group having 1 to 6 carbon atoms, an alkenyl group having 2 to 6 carbon atoms, an alkyl halide group having 1 to 6 carbon atoms, a substituted amino group, an alkoxy group having 1 to 6 carbon atoms, a nitro group, an aryl group, a —C(=O)—OR group, or an —SO$_2$R group, and R is an alkyl group having 1 to 6 carbon atoms or an aryl group having 6 to 14 carbon atoms, the oxazole group is optionally substituted with one substituent or a plurality of identical or different substituents selected from a halogen atom, a cyano group, an alkyl group having 1 to 6 carbon atoms, an alkenyl group having 2 to 6 carbon atoms, an alkyl halide group having 1 to 6 carbon atoms, a substituted amino group, an alkoxy group having 1 to 6 carbon atoms, a nitro group, a —C(=O)—OR group, or an —SO$_2$R group, and R is an alkyl group having 1 to 6 carbon atoms or an aryl group having 6 to 14 carbon atoms, the quinoline group is optionally substituted with one substituent or a plurality of identical or different substituents selected from a cyano group, an alkyl group having 1 to 6 carbon atoms, an alkenyl group having 2 to 6 carbon atoms, an alkyl halide group having 1 to 6 carbon atoms, a substituted amino group, an alkoxy group having 1 to 6 carbon atoms, a nitro group, an aryl group, a —C(=O)—OR group, or an —SO$_2$R group, and R is an alkyl group having 1 to 6 carbon atoms or an aryl group having 6 to 14 carbon atoms, $A^y$ is a hydrogen atom, a substituted or unsubstituted alkyl group having 1 to 18 carbon atoms, a substituted or unsubstituted cycloalkyl group, a substituted or unsubstituted alkenyl group having 2 to 18 carbon atoms, or an organic group having 2 to 30 carbon atoms that includes at least one aromatic ring selected from the group consisting of an aromatic hydrocarbon ring and an aromatic hetero ring, provided that the aromatic ring included in $A^y$ is substituted or unsubstituted, and $A^x$ and $A^y$ optionally bond to each other to form a ring, and Q is a hydrogen atom.

9. The compound according to claim 8, wherein the compound is selected from the group consisting of compounds (I-1) to (I-3) and (I-5) to (I-16):

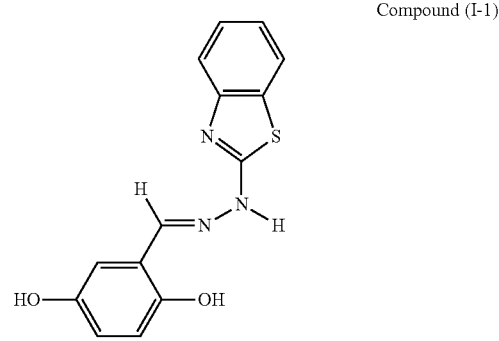

Compound (I-1)

Compound (I-2)
Compound (I-3)
Compound (I-5)
Compound (I-6)
Compound (I-7)
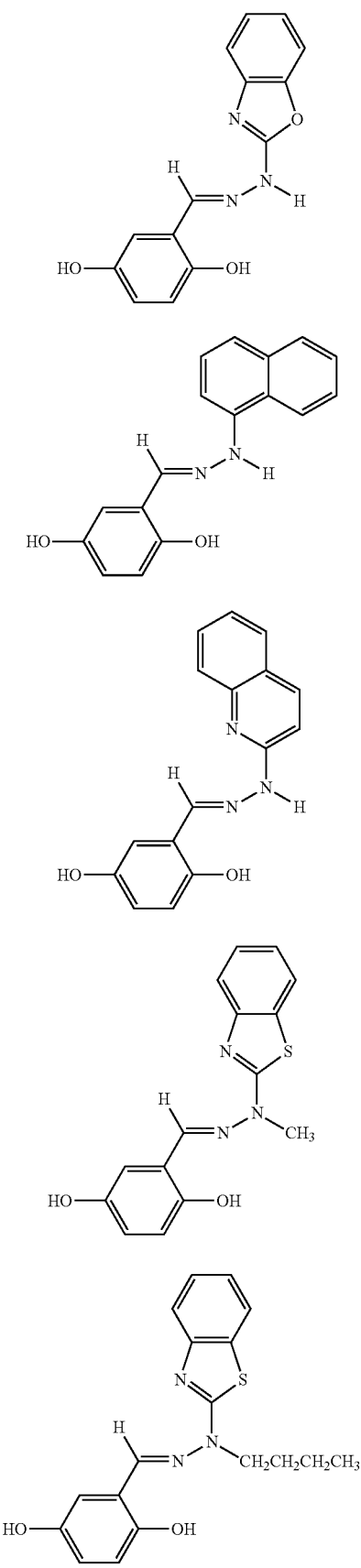
Compound (I-8)
Compound (I-9)
Compound (I-10)
Compound (I-11)
Compound (I-12)
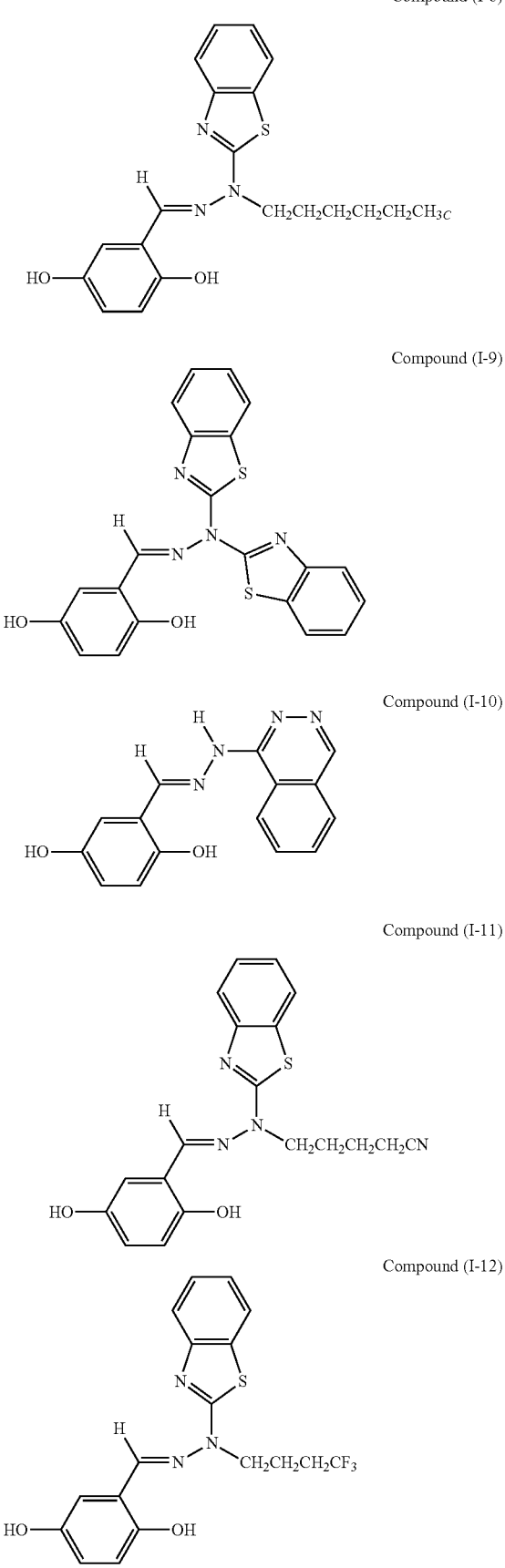

-continued
Compound (I-13)
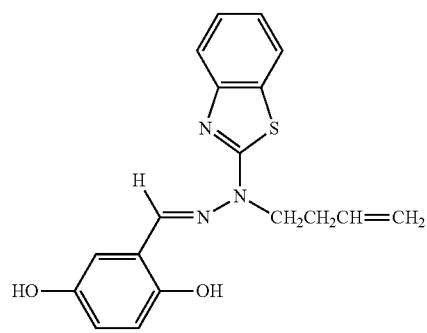
Compound (I-14)
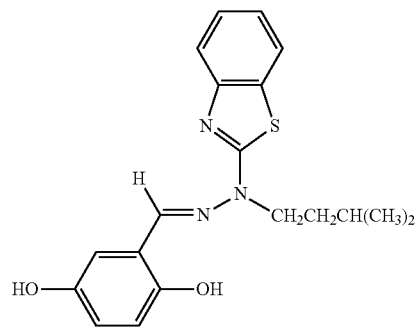
Compound (I-15)
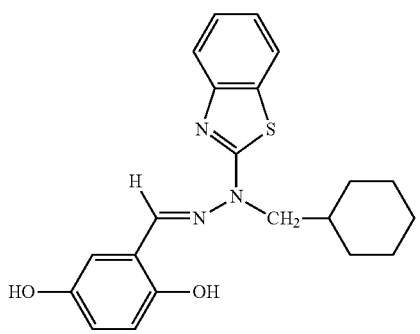
Compound (I-16)
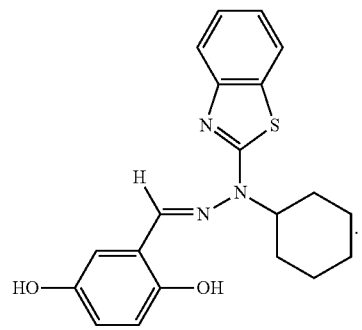
* * * * *